(12) United States Patent
Izvorski et al.

(10) Patent No.: US 10,792,495 B2
(45) Date of Patent: Oct. 6, 2020

(54) NEUROMODULATION DEVICE AND METHOD FOR USE

(71) Applicant: Thimble Bioelectronics, Inc., San Francisco, CA (US)

(72) Inventors: Alexander B. Izvorski, San Francisco, CA (US); Shaun Rahimi, San Francisco, CA (US); Kevin McCullough, San Francisco, CA (US)

(73) Assignee: Thimble Bioelectronics, Inc., San Francisco, CA (US)

( * ) Notice: Subject to any disclaimer, the term of this patent is extended or adjusted under 35 U.S.C. 154(b) by 0 days.

(21) Appl. No.: 15/649,468

(22) Filed: Jul. 13, 2017

(65) Prior Publication Data

US 2018/0154147 A1 Jun. 7, 2018

Related U.S. Application Data

(60) Provisional application No. 62/429,054, filed on Dec. 1, 2016.

(51) Int. Cl.
*A61N 1/36* (2006.01)
*A61N 1/04* (2006.01)

(52) U.S. Cl.
CPC ....... *A61N 1/36021* (2013.01); *A61N 1/0456* (2013.01); *A61N 1/0492* (2013.01); *A61N 1/36034* (2017.08); *A61N 1/36071* (2013.01)

(58) Field of Classification Search
CPC ............ A61N 1/36021; A61N 1/36034; A61N 1/0456; A61N 1/0492; A61N 1/36071
(Continued)

(56) References Cited

U.S. PATENT DOCUMENTS 3,012,271 A 12/1961 Morse
3,727,616 A 4/1973 Lenzkes
(Continued)

FOREIGN PATENT DOCUMENTS

CA 2337214 1/2000
CA 2290058 5/2000
(Continued)

OTHER PUBLICATIONS

Hughes, G.S. et al. "Response of plasma beta-endorphins to transcutaneous electrical nerve stimulation in healthy subjects," *Physical Therapy*, 64(7):1062-1066, Jul. 1, 1984.
(Continued)

*Primary Examiner* — Erin M Piateski
(74) *Attorney, Agent, or Firm* — Levine Bagade Han LLP

(57) ABSTRACT

Neuromodulation devices and methods of their use are described in which a therapeutic device is configured to generate a treatment for treating pain such as the reduction of the symptoms of chronic and acute pain as well as for treating other conditions. The neuromodulation device generates an output electrical signal in the form of pulses with a fast rise-time spike waveform followed by a longer-duration, lower amplitude primary phase waveform. The output signal includes a broad range of frequency components, with time constants tuned so as to interact with specific cell membrane or cellular components. The output signal may be conducted to the patient via electrodes. The pulses are triggered at variable intervals which prevent habituation.

43 Claims, 11 Drawing Sheets

(58) Field of Classification Search
USPC .......................................................... 607/46
See application file for complete search history.

(56) References Cited

U.S. PATENT DOCUMENTS

| | | | |
|---|---|---|---|
| 3,835,833 A | 9/1974 | Limoge | |
| 4,071,033 A | 1/1978 | Nawracaj et al. | |
| 4,230,121 A | 10/1980 | Stanton | |
| 4,323,073 A | 4/1982 | Ferris | |
| 4,340,063 A | 7/1982 | Maurer | |
| 4,398,545 A | 8/1983 | Wilson | |
| 4,682,601 A | 7/1987 | Tagliavini | |
| 4,693,254 A | 9/1987 | Mickiewicz et al. | |
| 4,754,759 A | 7/1988 | Allocca | |
| 4,763,656 A | 8/1988 | Nauman | |
| 4,803,988 A | 2/1989 | Thomson | |
| 4,865,048 A | 9/1989 | Eckerson | |
| 4,887,603 A | 12/1989 | Morawetz et al. | |
| 4,922,908 A | 5/1990 | Morawetz et al. | |
| 5,036,850 A | 8/1991 | Owens | |
| 5,063,929 A | 11/1991 | Bartelt et al. | |
| 5,065,083 A | 11/1991 | Owens | |
| 5,117,826 A | 6/1992 | Bartelt et al. | |
| 5,211,175 A | 5/1993 | Gleason et al. | |
| 5,395,398 A | 3/1995 | Rogozinski | |
| 5,421,817 A | 6/1995 | Liss et al. | |
| 5,458,625 A | 10/1995 | Kendall | |
| 5,507,781 A * | 4/1996 | Kroll .................... | A61N 1/3956 607/5 |
| 5,512,057 A | 4/1996 | Reiss et al. | |
| 5,514,165 A | 5/1996 | Malaugh et al. | |
| 5,571,149 A | 11/1996 | Liss et al. | |
| 5,593,432 A | 1/1997 | Crowther et al. | |
| 5,607,453 A | 3/1997 | Ishiguro et al. | |
| 5,725,563 A * | 3/1998 | Klotz ................. | A61N 1/36014 607/62 |
| 5,851,223 A | 12/1998 | Liss et al. | |
| 5,885,219 A | 3/1999 | Nightengale | |
| 5,899,922 A | 5/1999 | Loos | |
| 6,023,642 A | 2/2000 | Shealy et al. | |
| 6,064,911 A | 5/2000 | Wingrove | |
| 6,161,044 A | 12/2000 | Silverstone | |
| 6,351,674 B2 | 2/2002 | Silverstone | |
| 6,438,418 B1 | 8/2002 | Swerdlow et al. | |
| 6,567,702 B1 | 5/2003 | Nekhendzy et al. | |
| 6,701,189 B2 | 3/2004 | Fang et al. | |
| 6,718,202 B2 | 4/2004 | Mann et al. | |
| 6,871,092 B2 | 3/2005 | Piccone | |
| 6,937,893 B2 | 8/2005 | Danz et al. | |
| 7,027,860 B2 | 4/2006 | Bruninga et al. | |
| 7,117,034 B2 | 10/2006 | Kronberg | |
| 7,326,181 B2 | 2/2008 | Katims | |
| 7,587,245 B2 | 9/2009 | Kivlighan | |
| RE41,045 E | 12/2009 | Sluijter et al. | |
| 7,699,768 B2 | 4/2010 | Kishawi et al. | |
| 7,725,193 B1 | 5/2010 | Chu | |
| 7,742,810 B2 | 6/2010 | Moffitt et al. | |
| 7,753,836 B2 | 7/2010 | Peterchev | |
| 7,844,339 B2 | 11/2010 | Buchner | |
| 7,946,973 B2 | 5/2011 | Peterchev | |
| 8,046,077 B2 | 10/2011 | York et al. | |
| 8,046,082 B2 | 10/2011 | Herregraven et al. | |
| 8,086,318 B2 | 12/2011 | Strother et al. | |
| RE43,374 E | 5/2012 | Kronberg | |
| 8,255,057 B2 | 8/2012 | Fang et al. | |
| 8,315,711 B2 | 11/2012 | Campos et al. | |
| 8,428,735 B2 | 4/2013 | Littlewood et al. | |
| 8,478,410 B2 | 7/2013 | Kivlighan | |
| 8,676,324 B2 | 3/2014 | Simon et al. | |
| 8,870,773 B2 | 10/2014 | Narouze | |
| 8,880,178 B2 | 11/2014 | Popovic et al. | |
| 8,897,870 B2 | 11/2014 | De | |
| 9,037,248 B2 | 5/2015 | Durand et al. | |
| 9,101,766 B2 | 8/2015 | Nekhendzy | |
| 9,144,681 B2 | 9/2015 | Decre et al. | |
| 9,248,274 B2 | 2/2016 | Troosters et al. | |
| 9,265,941 B2 | 2/2016 | Van et al. | |
| 9,283,387 B2 | 3/2016 | Thacker et al. | |
| 9,327,126 B2 | 5/2016 | Alataris et al. | |
| 9,399,134 B2 | 7/2016 | Simon et al. | |
| 9,440,069 B2 | 9/2016 | Liu | |
| 9,440,077 B2 | 9/2016 | Popovic et al. | |
| 9,526,892 B2 | 12/2016 | Thompson et al. | |
| 9,592,380 B2 | 3/2017 | Popovic et al. | |
| 9,895,539 B1 | 2/2018 | Heit et al. | |
| 2002/0026226 A1 | 2/2002 | Ein | |
| 2002/0188331 A1 | 12/2002 | Fang et al. | |
| 2002/0193844 A1 | 12/2002 | Michelson et al. | |
| 2004/0131998 A1 | 7/2004 | Marom et al. | |
| 2004/0210254 A1 | 10/2004 | Burnett et al. | |
| 2004/0260359 A1 | 12/2004 | Osrud | |
| 2004/0267333 A1 * | 12/2004 | Kronberg ............... | A61N 1/326 607/72 |
| 2005/0033381 A1 | 2/2005 | Carter et al. | |
| 2005/0033387 A1 | 2/2005 | Buchner | |
| 2005/0245977 A1 | 11/2005 | Varrichio et al. | |
| 2005/0245989 A1 | 11/2005 | Davis | |
| 2006/0009820 A1 | 1/2006 | Royle | |
| 2006/0025842 A1 | 2/2006 | Mochizuki | |
| 2007/0276449 A1 | 11/2007 | Gunter et al. | |
| 2007/0293917 A1 | 12/2007 | Thompson et al. | |
| 2008/0033504 A1 | 2/2008 | Bertolucci | |
| 2008/0097564 A1 | 4/2008 | Lathrop | |
| 2008/0103496 A1 | 5/2008 | Christopherson et al. | |
| 2008/0103558 A1 | 5/2008 | Wenzel et al. | |
| 2008/0146921 A1 | 6/2008 | Novak et al. | |
| 2008/0167697 A1 | 7/2008 | Johnson | |
| 2009/0018462 A1 | 1/2009 | Bell | |
| 2009/0149782 A1 | 6/2009 | Cohen | |
| 2010/0016732 A1 | 1/2010 | Wells et al. | |
| 2010/0145399 A1 | 6/2010 | Johari et al. | |
| 2010/0324626 A1 | 12/2010 | Lefkovitz | |
| 2011/0022126 A1 | 1/2011 | Taylor | |
| 2011/0093033 A1 * | 4/2011 | Nekhendzy ......... | A61N 1/36017 607/46 |
| 2011/0178571 A1 | 7/2011 | Tannebaum et al. | |
| 2011/0192398 A1 | 8/2011 | Euliano et al. | |
| 2011/0288616 A1 | 11/2011 | Moore et al. | |
| 2012/0109241 A1 | 5/2012 | Rauscher | |
| 2013/0090712 A1 * | 4/2013 | Popovic ............. | A61N 1/36003 607/148 |
| 2013/0197604 A1 | 8/2013 | Marineo | |
| 2013/0226042 A1 | 8/2013 | Novak et al. | |
| 2013/0238070 A1 | 9/2013 | Deridder | |
| 2014/0018897 A1 | 1/2014 | Pastorelli | |
| 2014/0074000 A1 | 3/2014 | Liu | |
| 2014/0142654 A1 | 5/2014 | Simon et al. | |
| 2014/0163645 A1 | 6/2014 | Dinsmoor et al. | |
| 2014/0194771 A1 | 7/2014 | Parker et al. | |
| 2014/0316298 A1 | 10/2014 | Thompson et al. | |
| 2014/0330335 A1 | 11/2014 | Errico et al. | |
| 2014/0350327 A1 | 11/2014 | Poon et al. | |
| 2014/0371515 A1 | 12/2014 | John | |
| 2015/0088212 A1 | 3/2015 | De | |
| 2015/0094790 A1 | 4/2015 | Shishilla et al. | |
| 2015/0127065 A1 | 5/2015 | Pastorelli | |
| 2015/0216588 A1 | 8/2015 | Deem et al. | |
| 2015/0246248 A1 | 9/2015 | Wagner | |
| 2015/0257970 A1 | 9/2015 | Mücke et al. | |
| 2015/0265836 A1 | 9/2015 | Simon et al. | |
| 2015/0273215 A1 | 10/2015 | Nabutovsky et al. | |
| 2015/0273234 A1 | 10/2015 | Weinstock | |
| 2015/0374985 A1 | 12/2015 | Fahey | |
| 2016/0008620 A1 | 1/2016 | Stubbeman | |
| 2016/0015988 A1 | 1/2016 | Perryman et al. | |
| 2016/0051817 A1 | 2/2016 | Popovic et al. | |
| 2016/0114181 A1 | 4/2016 | Vaynberg et al. | |
| 2016/0121116 A1 | 5/2016 | Simon et al. | |
| 2016/0136423 A1 | 5/2016 | Simon et al. | |
| 2016/0144175 A1 | 5/2016 | Simon et al. | |
| 2016/0151628 A1 | 6/2016 | Simon et al. | |
| 2016/0213952 A1 | 7/2016 | Zovrin et al. | |
| 2016/0236004 A1 | 8/2016 | Fischell et al. | |
| 2016/0243359 A1 | 8/2016 | Sharma | |

(56) References Cited

U.S. PATENT DOCUMENTS

| | | | |
|---|---|---|---|
| 2016/0287869 A1 | 10/2016 | Errico et al. |
| 2016/0287878 A1 | 10/2016 | Bradley et al. |
| 2016/0310198 A1 | 10/2016 | Newman |
| 2016/0346542 A1 | 12/2016 | Simon et al. |
| 2016/0367823 A1 | 12/2016 | Cowan et al. |
| 2016/0375256 A1 | 12/2016 | Cigaina et al. |

FOREIGN PATENT DOCUMENTS

| | | |
|---|---|---|
| CA | 2194777 | 11/2000 |
| CA | 2312071 | 1/2001 |
| CA | 2530396 | 1/2005 |
| CA | 2118241 | 7/2005 |
| CA | 2797078 | 11/2011 |
| CA | 2816962 | 5/2012 |
| CN | 1986105722 | 1/1987 |
| CN | 100478042 | 4/2009 |
| CN | 101415463 | 4/2009 |
| CN | 101516440 | 8/2009 |
| CN | 101721200 | 6/2010 |
| CN | 1842356 | 5/2011 |
| CN | 101437572 | 8/2012 |
| CN | 101522257 | 10/2013 |
| CN | 102256662 | 1/2014 |
| CN | 104474633 | 4/2015 |
| CN | 102145205 | 9/2015 |
| DE | 102007012474 | 5/2010 |
| EP | 9920 | 4/1980 |
| EP | 99662 | 2/1984 |
| EP | 143748 | 6/1985 |
| EP | 171881 | 2/1986 |
| EP | 173419 | 3/1986 |
| EP | 268366 | 5/1988 |
| EP | 414248 | 2/1991 |
| EP | 557562 | 9/1993 |
| EP | 616546 | 9/1994 |
| EP | 759307 | 2/1997 |
| EP | 1377343 | 1/2004 |
| EP | 1526892 | 5/2005 |
| EP | 1575665 | 11/2006 |
| EP | 1985332 | 10/2008 |
| EP | 2089108 | 8/2009 |
| EP | 2269688 | 1/2011 |
| EP | 2308551 | 4/2011 |
| EP | 2490635 | 8/2012 |
| EP | 2550060 | 1/2013 |
| EP | 2841150 | 3/2015 |
| EP | 2942023 | 11/2015 |
| EP | 1171189 | 5/2016 |
| ES | 2241881 | 11/2005 |
| ES | 2338247 | 5/2010 |
| FR | 2500309 | 8/1982 |
| FR | 2627918 | 9/1989 |
| GB | 1477095 | 6/1977 |
| GB | 2177304 | 1/1987 |
| JP | 02908019 | 6/1999 |
| JP | 2006212458 | 8/2006 |
| JP | 2007524463 | 8/2007 |
| JP | 2009504258 | 2/2009 |
| JP | 2013042976 | 3/2013 |
| JP | 05323935 | 10/2013 |
| JP | 2014012200 | 1/2014 |
| JP | 2014168698 | 9/2014 |
| JP | 2015123376 | 7/2015 |
| KR | 2006040594 | 5/2006 |
| KR | 2012099146 | 9/2012 |
| WO | WO 1991/006340 | 5/1991 |
| WO | WO 1992/006737 | 4/1992 |
| WO | WO 1994/017855 | 8/1994 |
| WO | WO 1997/038751 | 10/1997 |
| WO | WO 2000/056395 | 1/2002 |
| WO | WO 2002/018008 | 3/2002 |
| WO | WO 2001/003768 | 7/2002 |
| WO | WO 2002/094375 | 11/2002 |
| WO | WO 2003/022354 | 3/2003 |
| WO | WO 2004/060481 | 7/2004 |
| WO | WO 2004/067087 | 8/2004 |
| WO | WO 2004/084747 | 10/2004 |
| WO | WO 2005/007029 | 1/2005 |
| WO | WO 2005/065770 | 7/2005 |
| WO | WO 2006/000015 | 1/2006 |
| WO | WO 2007/056474 | 5/2007 |
| WO | WO 2007/056475 | 7/2007 |
| WO | WO 2007/136713 | 11/2007 |
| WO | WO 2007/141874 | 12/2007 |
| WO | WO 2008/030656 | 3/2008 |
| WO | WO 2008/145724 | 12/2008 |
| WO | WO 2009/054845 | 4/2009 |
| WO | WO 2009/058984 | 5/2009 |
| WO | WO 2010/047834 | 4/2010 |
| WO | WO 2011/041203 | 4/2011 |
| WO | WO 2011/044159 | 4/2011 |
| WO | WO 2012/030522 | 3/2012 |
| WO | WO 2012/144713 | 10/2012 |
| WO | WO 2013/126176 | 8/2013 |
| WO | WO 2014/083203 | 6/2014 |
| WO | WO 2014/197628 | 12/2014 |
| WO | WO 2015/086873 | 6/2015 |
| WO | WO 2015/138981 | 9/2015 |
| WO | WO 2015/144758 | 10/2015 |
| WO | WO 2015/158379 | 10/2015 |
| WO | WO2015/175570 * 11/2015 ............ A61N 1/327 |
| WO | WO 2015/175570 | 11/2015 |
| WO | WO 2015/179571 | 11/2015 |
| WO | WO 2016/032929 | 3/2016 |
| WO | WO 2016/032931 | 3/2016 |
| WO | WO 2016/040961 | 3/2016 |
| WO | WO 2016/057855 | 4/2016 |
| WO | WO 2018/101986 | 6/2018 |

OTHER PUBLICATIONS

Salar, G. et al. "Effect of transcutaneous electrotherapy on CSF β-endorphin content in patients without pain problems," *Pain*, 10(2):169-172, Apr. 1981.

Caliandro, P. et al. "Jitter of Corticospinal Neurons During Repetitive Transcranial Magnetic Stimulation. Method and Possible Clinical Implications," *Brain Stimulation*, 7:580-586, May 2014.

Pethig, "Electrical Properties of Biological Tissue, Chapter 6," Modern Bioelectricity, Andrew A. Marino (ed), Marcel Dekker, New York, 1988.

Liu, DS, et al. "Activation of Na+ and K+ pumping modes of (Na, K)-ATPase by an oscillating electric field," *Journal of Biological Chemistry*, 265(13):7260-7267, May 5, 1990.

Melzack, R. et al. "Pain Mechanisms: A New Theory," *Science*, 150(3699):971-979, Nov. 19, 1965.

Sluka, K. et al. "Transcutaneous Electrical Nerve Stimulation: Basic Science Mechanisms and Clinical Effectiveness," *Journal of Pain*, 4(3):109-121, Apr. 2003.

\* cited by examiner

NEUROMODULATION DEVICE AND METHOD FOR USE

CROSS-REFERENCE TO RELATED APPLICATIONS

This application claims the benefit of priority to U.S. Provisional Patent Application No. 62/429,054 filed Dec. 1, 2016, which is incorporated herein by reference in its entirety.

FIELD OF THE INVENTION

The present invention relates to methods and apparatus for electrical neuromodulation. More particularly, the present invention relates to methods and apparatus for electrical neuromodulation for treating symptoms of chronic and acute pain as well as other conditions.

BACKGROUND OF THE INVENTION

Pain is the mental manifestation of a neurological response to various physiological and psychological ailments. Pain serves as a warning of physical injury or biological dysfunction. Sometimes pain persists much longer than it takes for the healing of the initial injury to occur, and may be very difficult to alleviate. The most common pain relief methods employ drugs (e.g., opioids) that act to block neurotransmission pathways within the body. Often such drugs are not effective for pain relief over the long term, or produce unacceptable side effects. Consequently, various forms of electrical stimulation such as spinal cord stimulation (SCS) and transcutaneous electrical nerve stimulation (TENS) have also been employed to alleviate pain.

SCS is effective but is an invasive procedure and has all the typical risks associated with implantable devices, as well as the risk of serious damage to the spinal cord. TENS is not effective in all patients due to the difficulty in picking effective settings and it may produce effects which only last during stimulation and do not produce long term pain relief.

Accordingly, there is a need for methods and devices which do not carry the risks of drug side effects, surgical risks, and which are also effective and produce long term pain relief.

SUMMARY OF THE INVENTION

A novel neuromodulation device is provided which generates an output signal in the form of pulses with a fast rise-time spike waveform followed by a longer-duration, lower amplitude primary phase waveform. The timing of the parts of the pulses is tuned to the time constants of certain cellular or cell membrane components, and induces conformational changes which result in modified function of those components of nerve fibers, as opposed to previously known forms of nerve stimulation which cause depolarization of nerve fibers. The waveform and its parameters also prevent habituation of the treatment stimulation by the patient thereby enabling longer-term application of treatments while maintaining effectiveness. The output signal may be provided to a patient via electrodes which are placed on the patient in an appropriate location to provide pain relief. The output signal may also be used to treat other conditions such as inflammation, or to speed up wound healing.

One variation for a neuromodulation treatment apparatus may generally comprise a controller programmed to transmit one or more pulse waveforms having a spike and a primary phase following the spike, wherein the spike has a first amplitude and a first duration time and the primary phase has a second amplitude and a second duration time, and wherein the first amplitude is greater than the second amplitude and the first duration time is less than the second duration time such that the spike has an intensity which is greater than an average intensity of the primary phase.

One variation for a method of neuromodulation treatment may generally comprise positioning one or more electrodes in proximity to a tissue region of interest, transmitting a spike of at least one pulse waveform through the one or more electrodes, the spike having a first amplitude and a first duration time, and transmitting a primary phase of the at least one pulse waveform following the spike through the one or more electrodes, the primary phase having a second amplitude and a second duration time, wherein the first amplitude is greater than the second amplitude and the first duration time is less than the second duration time such that the spike has an intensity which is greater than an average intensity of the primary phase.

One variation of the neuromodulation device may generally comprise a control electronics module which may be programmable to provide the desired pulse signals to the patient. The control electronics module may include the various electronics which are used to effect the treatment, e.g., timers, clocks, DACs, etc. which control the output on/off state, pulse amplitude, timing, modulation, and other pulse parameters. A control module may be in communication with the control electronics module through any number of interface mechanisms, e.g., buttons, knobs, sliders, capacitive touch sensors, etc. through which a user can turn the device on/off, adjust amplitude or other settings, etc. Additionally, the control module or other controller may communicate locally or remotely with the control electronics module through a communication interface module which may include any number of various wired and/or wireless communication mechanisms, e.g., Bluetooth®, Bluetooth® Low Energy or Bluetooth® Smart (Bluetooth SIG, Inc., Kirkland. Wash.), ANT, ZigBee, WiFi, infrared (e.g., Infrared Data Association (IrDA) associated wireless communications, etc.

The control electronics module may provide any number of details, feedback, or information about its operation through an indicator module which may include any variety of indicators, e.g., LEDs or indicator lights, displays such as LCD displays, segment displays, etc., which may be positioned directly upon the neuromodulation device or separately in communication with the control electronics.

In order for the neuromodulation device to provide the electrical stimulation to the patient's body, the control electronics may be in communication with a pulse generating electronics module which is in communication with an electrode module through a connecting elements module. The pulse generating electronics module may include various components, e.g., amplifiers, op-amps, output filtering or pulse shaping circuits, output limiting or sensing and feedback circuits, elements which provide galvanic isolation, DC blocking, etc., which are configured to produce the electric pulses with controlled shape and amplitude as described herein.

The electrodes module electrically coupled to the pulse generating electronics module may be shaped in various configurations for facilitating placement upon the patient depending upon the region of the body to be treated. Accordingly, the electrodes may be external, transcutaneous, internal, or implantable, for providing an electrical connection from the device output to the body, particularly to the target tissues or nerves.

Using the neuromodulation device described, the control electronics module may be programmed to effect a specified pulse waveform generated by the pulse generating electronics module and transmitted through the electrodes and to the area of the patient's body upon which the electrodes are positioned for treatment. Generally, the pulse waveform may have a primary phase followed by an optional dead time period and then a secondary phase. Initiating the primary phase is a leading edge 3 having a relatively fast rise time which leads to a spike having an intensity significantly greater than an average intensity of the primary phase. The remainder of the primary phase may have an intensity which is significantly lower than the intensity of the spike.

The dead time period, if included, may have an output amplitude of zero. If the dead time period is omitted, the secondary phase may follow immediately after the primary phase where the secondary phase may have a polarity opposite to that of the primary phase. Like the dead time period, the secondary phase may be optionally omitted entirely from the pulse waveform. The treatment pulses having the pulse waveform may be repeated during a treatment where a specified time interval may be present between each individual pulse waveform.

The spike itself may be shaped as, e.g., a half-sine wave, sinc, parabolic, or similar waveform, as it is not necessary for it to have a constant level (e.g., "flat top"), although it is desirable if the slew rate during most of the rising edge is relatively constant.

Additionally, the transitions between the spike, primary, dead time, secondary, and OFF do not need to have rapid rise and fall times, or in any case the rapid rise and fall times are not necessary for effectiveness. However, it is desirable to have a relatively rapid and/or fall time at the end of the spike to maximize patient comfort. Once the brief time at maximum amplitude during the spike has passed, it is unlikely that any high but sub-maximum amplitude would have a physiological effect; however, it may cause greater charging of the skin capacitance and thus skin discomfort and for that reason it is desirable for the spike to transition to the lower level during the remainder of the primary phase relatively quickly. The fall time at the end of the primary phase, the rise time from the dead time to the secondary phase, and the fall time from secondary phase to the OFF state or inter-pulse interval are even less critical, and correspondingly the exact shape or slew rate during those parts of the pulse waveform may be implemented in different ways while still having a therapeutically effective pulse shape as described herein.

Turning now to the individual portions of the pulse waveform, the spike is comprised of a relatively high amplitude, short duration spike which has a leading edge with a fast rise time. The effective electric field during the spike is expected to be high enough to be able to drive conformational changes of the cellular components which are targeted therapeutically directly, by the electrostatic forces acting on fixed charges or dipoles therein.

The spike is specifically not necessarily intended to cause depolarization of nerve fibers as the threshold for nerve fiber depolarization by short electric field pulses is between, e.g., 0.75-2.98e-3 V-s/m (depending on fiber diameter). An effective spike may have an amplitude of up to, e.g., 80-100 V, applied over the inter-electrode distance of, e.g., 5-20 cm, and duration of less than 10 us, or a duration of, e.g., 1-5 us, producing a sub-threshold value of less than, e.g., 0.01e-3 V-s/m, which is two orders of magnitude lower than that required for depolarization. Even a very intense spike of, e.g., 1 kV peak for 1 us, with a close electrode spacing of, e.g., 1 cm, has a sub-threshold value of, e.g., 0.1e-3 V-s/m, which is an order of magnitude lower than required for depolarization.

The peak spike amplitude which may be safely used may be limited by the possibility of electroporation, and (in the case of high pulse repetition rates) by total pulse energy delivered to tissue. The electroporation threshold may be higher than, e.g., 1 kV/cm for pulses of 100 us or shorter duration. Much lower spike-induced field strengths, on the order of, e.g., 8-50 V/cm, are found to be therapeutically effective.

In one embodiment, the leading edge of the spike has a controlled slew rate, such that the rise time of the leading edge corresponds to the time constant for the conformational changes of the target cellular components. The controlled slew rate allows any mobile charges (e.g., ions, molecular dipoles, etc.) with substantially shorter time constants to be mostly or substantially completely polarized by the applied field, and any charges with longer time constants to not be polarized yet, leading to maximum effect for a certain level of applied energy. The rise time is typically less than, e.g., 1 us, when targeting cellular membrane components, and more typically in the range of, e.g., 100-300 ns for pain relief. Significantly shorter rise times of less than, e.g., 50-100 ns, may be used to target intracellular components, for example in the nuclear membrane or mitochondrial membrane.

Following the spike, the remainder of the primary phase of the pulse is less likely to be able to directly drive conformational changes, since the amplitude is relatively too low, and also various capacitances such as skin capacitance or electric double layer capacitance at cell membranes have had sufficient time to charge or begin charging, thereby reducing the effective field in the vicinity of the target macromolecules.

However, while the primary phase may be important for optimum effect, a pulse which includes only the spike may be likely to be less effective. The primary phase also serves to maintain, rather than produce, the conformational changes. If the spike has a field which is large enough that it can quickly move the charged parts of some macromolecules, the remainder of the primary phase has a weaker field which cannot move them quickly yet is sufficient to hold them in place.

In essence, the initial spike causes any desired conformational changes, and the electrical field during the rest of the primary phase maintains the changed conformation. Additionally, the maintenance of a field with the same polarity after the major conformational changes have occurred would cause the slower migration of counterions which would balance the charge redistribution caused by the conformational changes, and act to stabilize or "freeze in" the modified conformation for a longer period of time.

The average amplitude of the primary phase only needs to be a fraction of the peak amplitude of the spike. However, as the skin capacitance and electric double layer capacitances are charging throughout the primary phase, this accumulating charge reduces the effective field at the target cellular components, and thus the amplitude should not be set too low. Very long duration of the primary phase (e.g., 500-1000 us) may lead to direct activation of muscle fibers leading to involuntary muscle contractions, and high currents combined with medium to long duration may lead to charging of the skin capacitance to an uncomfortable level (e.g., >50V per electrode). In practice the primary phase amplitude and duration may be set as high as is tolerable to the user, from a sub-sensory (imperceptible) level to a "strong but comfortable" level with amplitude and duration similar to TENS.

In one embodiment, the primary phase average current is between, e.g., 1 and 100 mA, and the duration is between, e.g., 20 and 500 us. In yet another embodiment, the primary phase average current is between, e.g., 10 and 50 mA, and the duration is between, e.g., 80 and 120 us. These values are appropriate for medium sized electrodes with pad area, e.g., 25-50 cm$^2$, spaced, e.g., 5-10 cm apart. These values may be modified to maintain similar current density and field strength if the electrode configuration changes significantly.

During the secondary phase (if present), the direction of the electrical field is reversed to allow for a controlled discharge of the skin and tissue capacitances and so that a net charge per pulse may be minimized ("zero net charge per pulse"). A non-zero net charge per pulse is a concern because of the possibility for ions (e.g., metal ions from the electrodes) to migrate into the tissue over time (via iontophoresis), causing a negative physiological reaction. There is also a concern about the undesired migration of ions which are found in tissue, e.g., ions which have a signaling function such as calcium, diacylglycerol, inositol triphosphate, etc. as well as various charged proteins (especially those with high charge/mass ratio).

Additionally, for patient comfort it is desirable to discharge the skin capacitance faster that it would normally self-discharge as leaving the skin capacitance charged to a high voltage for an extended period of time may lead to activation of cutaneous sensory receptors found in the dermis or epidermis, including the cutaneous mechanoreceptors, nociceptors and thermoreceptors. This can be perceived as a sensation of tingling, paraesthesia ("pins and needles"), pinching or burning sensation in the skin under the electrodes, which may be uncomfortable especially at high stimulation levels. To limit the skin sensation under the electrode and improve patient comfort, it is desirable to limit the voltage to which the skin capacitance is charged, and to limit the duration for which the skin capacitance remains charged by discharging it using the secondary phase of the pulse.

In another embodiment, during the secondary phase of the output pulse the device may act as a current-limited constant impedance or current-limited short circuit rather than a current source. This allows any capacitances which were charged during the primary phase (e.g., electrode-skin capacitance, or cell membrane capacitances in tissue) to discharge in a controlled way, without being able to drive new charges. This mode is shown in FIG. 4 (described in further detail below) where the current decays exponentially during the secondary phase, consistent with the relaxation behavior of an RC circuit provided by the load. In this example, the load resistance is high enough that the device current limit is not reached. If a lower resistance were connected then the device would limit current during part of the secondary phase. The secondary phase duration may be chosen to be long enough so that the ending voltage is near zero. With typical electrode and tissue parameters, a duration of, e.g., approximately 3-5 times the primary phase duration, allows for a near-zero ending voltage.

In another embodiment, the secondary phase of the output pulse may be a current source and the amplitude and duration may be chosen so that the net charge during the secondary phase is approximately equal to the net charge during the primary phase, and/or so that the residual voltage after the secondary phase is near zero.

The secondary phase amplitude may be chosen so as to allow relatively rapid discharge (for patient comfort) yet limit the peak currents. In another embodiment, the maximum amplitude during the secondary phase may be chosen to be approximately equal to the average amplitude during the primary phase.

If the secondary phase is not present, the skin and tissue capacitances may self-discharge once the application of the primary phase is removed. Since the self-discharge is relatively slower than the external or driven discharge (as would be provided by a secondary phase), this allows the effects of the electrical field to last longer (or tail off over a longer period) at the cost of potentially reduced patient comfort at high stimulation amplitudes. In another embodiment, the secondary phase may be omitted if the stimulation is at a very low or sub-sensory (imperceptible) amplitude.

In yet another example, the devices and methods described herein may be used to treat a number of various conditions such as treatment of pain including chronic or acute pain in human subjects. Examples of the types of pain which may be treated with the devices and methods herein may include, e.g., somatic pain, musculoskeletal pain, mechanical pain, neuropathic pain, phantom pain, inflammatory pain, postoperative pain, allodynia, complex regional pain syndrome, fibromyalgia, etc.

The degree and duration of pain relief may depend on the degree to which any underlying injury or other pathology has healed. In the case of acute injury, the pain relief may be only temporary and may require repeated or continuous treatment. On the other hand, in the case of chronic pain where the original injury is fully healed, treatment using the device and methods herein may provide durable pain relief.

Generally, during use two or more electrodes of the device may be placed upon the surface of the body such that the current between the electrodes passes through the painful area or through some of the major sensory nerves which innervate the painful area.

DETAILED DESCRIPTION OF THE INVENTION

A neuromodulation device is provided which generates an output signal in the form of pulses having a relatively fast rise-time spike waveform followed by a relatively longer-duration, lower amplitude primary phase waveform. The timing of the parts of the pulses is tuned to the time constants of certain cellular or cell membrane components, and induces conformational changes which result in a modified function of those components of nerve fibers rather than a depolarization of nerve fibers which occurs in other neuromodulation stimulation devices. The output signal may be provided to a patient via electrodes which may be placed on the patient in an appropriate location to provide pain relief. The output signal may also be used to treat other conditions such as inflammation, or to speed up wound healing. The manner in which the pulses are configured and triggered at variable intervals prevents habituation of the treatment stimulation by a patient thereby enabling use of the devices and methods described herein for extended periods of time while maintaining treatment effectiveness.

Neuromodulation Device

Figure 1:
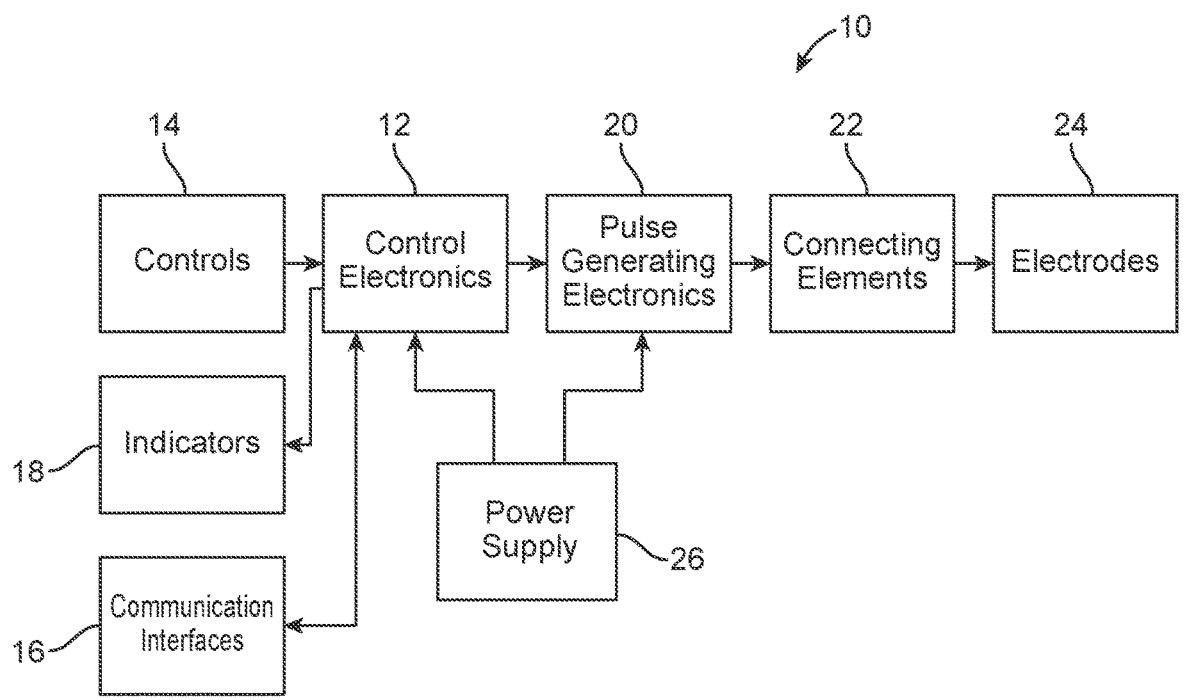
FIG. 1 shows a block diagram illustrating modules of one variation of the neuromodulation device.

As shown in FIG. 1, one variation of the neuromodulation device is illustrated as a block diagram 10 to show the different modules of the device. The control electronics module 12 generally comprises a microcontroller which may be programmable to provide the desired pulse signals to the patient. The control electronics module 12 may also include the various electronics which are used to effect the treatment, e.g., timers, clocks, DACs, etc. which control the output on/off state, pulse amplitude, timing, modulation, and other pulse parameters. In order to actuate and/or interface with the control electronics module 12, a control module 14 may be in communication with the control electronics module 12 through any number of interface mechanisms, e.g., buttons, knobs, sliders, capacitive touch sensors, etc. through which a user can turn the device on/off, adjust amplitude or other settings, etc. Additionally, the control module 14 or other controller may communicate locally or remotely with the control electronics module 12 through a communication interface module 16 which may include any number of various wired and/or wireless communication mechanisms, e.g., Bluetooth®, Bluetooth® Low Energy or Bluetooth® Smart (Bluetooth SIG, Inc., Kirkland, Wash.), ANT, ZigBee, WiFi, infrared (e.g., Infrared Data Association (IrDA) associated wireless communications, etc.

The control electronics module 12 may provide any number of details, feedback, or information about its operation through an indicator module 18 which may include any variety of indicators, e.g., LEDs or indicator lights, displays such as LCD displays, segment displays, etc., which may be positioned directly upon the neuromodulation device or separately in communication with the control electronics 12.

In order for the neuromodulation device to provide the electrical stimulation to the patient's body, the control electronics 12 may be in communication with a pulse generating electronics module 20 which is in communication with an electrode module 24 through a connecting elements module 22. The control electronics module 12 and pulse generating electronics module 20 may be in communication with a power supply module 26 which supplies the power for the electrical stimulation. The power supply module 26 may comprise, e.g., a lithium ion battery with associated circuits such as voltage regulators, LDOs, boost or buck converters, etc. The device output may utilize a voltage which is much higher than that available from the battery, and therefore the power supply may optionally include a generating mechanism for providing the high voltage as well as regulated low voltages for the other internal circuits.

The pulse generating electronics module 20 may include various components, e.g., amplifiers, op-amps, output filtering or pulse shaping circuits, output limiting or sensing and feedback circuits, elements which provide galvanic isolation, DC blocking, etc., which are configured to produce the electric pulses with controlled shape and amplitude as described herein.

Each of the various components may be in electrical communication through the connecting elements module 22. The connecting elements used may comprise any number of electrically conductive elements, e.g., connectors, printed conductive traces, flex circuit boards, etc., which provide electrical connection from the electronics to the electrodes or between any number of electrical components.

The electrodes module 24 electrically coupled to the pulse generating electronics module 20 may be shaped in various configurations for facilitating placement upon the patient depending upon the region of the body to be treated. Accordingly, the electrodes may be external, transcutaneous, internal, or implantable, for providing an electrical connection from the device output to the body, particularly to the target tissues or nerves.

External electrodes, in one variation, may be constructed of a conductive current-distributing element, an electrochemical electrode interface (such as a silver chloride coated silver, stainless steel, graphite, etc.) at which an electrochemical reaction may occur and a hydrogel (such as polyacrylamide or other stable and biocompatible gel with good adhesion) which contains a conductive solution (typically sodium chloride). However, the electrodes may be chosen from any type of electrodes known in the art, based on biocompatibility, adhesion, comfort, current uniformity, durability, etc. The electrodes may be a driven as a pair of electrodes where the current flows from a first electrode to a second electrode, or as a more complex multi-polar setup, e.g., in a quadrupolar setup, with four electrodes driven as any one of six alternating pairs.

In other variations, the neuromodulation device may additionally and/or optionally include additional features or elements. For example, in one variation, the device may be controlled entirely via a communication interface using, e.g., wireless communication from a controller located remotely from the neuromodulation device. Such remotely located controllers may include, e.g., smartphones or other programmable devices, which may communicate via any number of wireless communication protocols, e.g., Bluetooth® Low Energy interface. Such a variation may remove the need for any controls or indicators on the device itself as the controls module 14 may be located remotely. In yet another alternative, the device may directly incorporate the controls module 14 upon the neuromodulation device itself so that it may be controlled entirely through an interface located upon the device.

Additionally and/or alternatively, the control electronics 12 and power supply 26 may be packaged as a compact device which may be removably attached as a unit upon electrodes 24 which are disposable, e.g., polyacrylamide hydrogel with silver ink conductive traces printed on a polymer film base. The electrodes 24 may be placed upon the region of interest upon the patient body and the device may be temporarily coupled to an engagement mechanism which also allows for the electrical communication between the pulse generating electronics 20 and the electrodes 24 to effect treatment upon the patient. This variation as well as others described may be combined in any number of combinations as practicable.

Electrical Pulse Waveform

Figure 2:
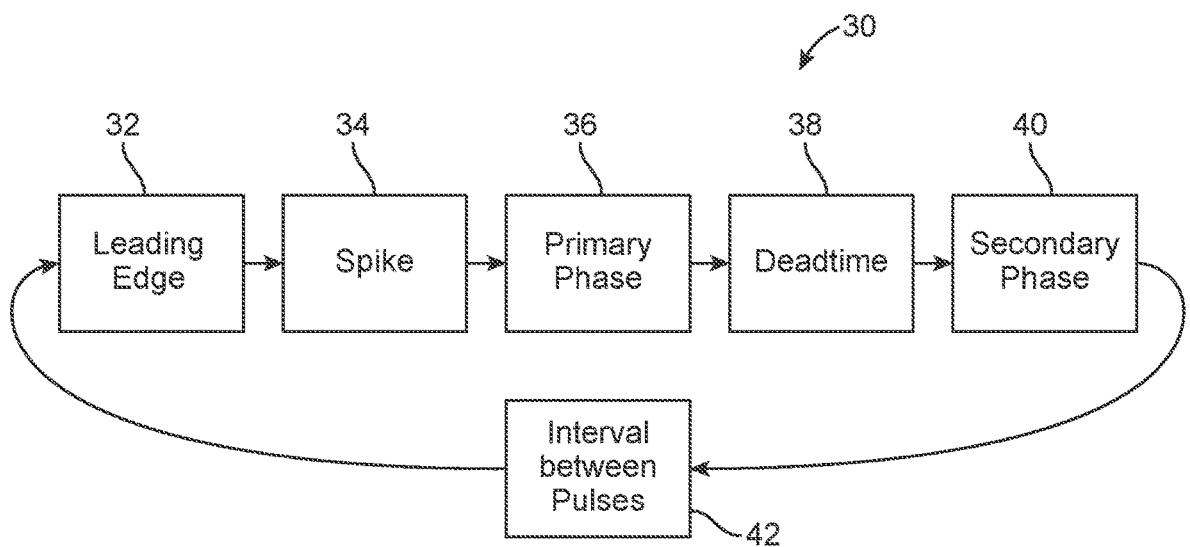
FIG. 2 shows a block diagram illustrating phases of one variation of an electrical pulse output by the neuromodulation device.

Using the neuromodulation device described, the control electronics module 12 may be programmed to effect a specified pulse waveform generated by the pulse generating electronics module 20 and transmitted through the electrodes 24 and to the area of the patient's body upon which the electrodes 24 are positioned for treatment. FIG. 2 shows a block diagram of a representative pulse waveform 30 illustrating the major phases of an electrical pulse output. Generally, the pulse waveform 30 may have a primary phase 36 followed by an optional dead time 38 period and then a secondary phase 40. Initiating the primary phase 36 is a leading edge 32 having a relatively fast rise time which leads to a spike 34 having an intensity significantly greater than an average intensity of the primary phase 36. The remainder of the primary phase 36 may have an intensity which is significantly lower than the intensity of the spike 34.

The dead time 38 period, if included, may have an output amplitude of zero. If the dead time 38 period is omitted, the secondary phase 40 may follow immediately after the primary phase 36 where the secondary phase 40 may have a polarity opposite to that of the primary phase 36. Like the dead time 38 period, the secondary phase 40 may be optionally omitted entirely from the pulse waveform 30. The treatment pulses having the pulse waveform 30 may be repeated during a treatment where a specified time interval 42 may be present between each individual pulse waveform 30.

While the output is described here in terms of amplitude, this may include a measure of either current or voltage. In one embodiment, the pulse waveforms 30 may be produced by a circuit which is a voltage-limited current source and the amplitudes may comprise current amplitudes. Using a current control allows for the effective movement of charges to be less dependent on the electrode impedance (which may change with skin condition or over time) and less dependent on the tissue impedance (which may change with placement or individually).

In another embodiment, the output may also comprise a voltage source or current-limited voltage source, since in the short term the tissue and electrode impedances are relatively constant and so the current is approximately equal to the voltage times a constant factor. In this case, the output may require more frequent adjustments. However controlled or produced, the amplitude pattern shown describes the variation in electrical field strength independent of the effects of variation in electrode impedance or the specifics of the control circuit.

If any parameters (such as timings or amplitude) of the output electrical pulses depend on the load impedance, they may be measured using a resistive-capacitive test load simulating the electrodes and human body, e.g., as described in the AAMI NS4 standard.

Figure 3:
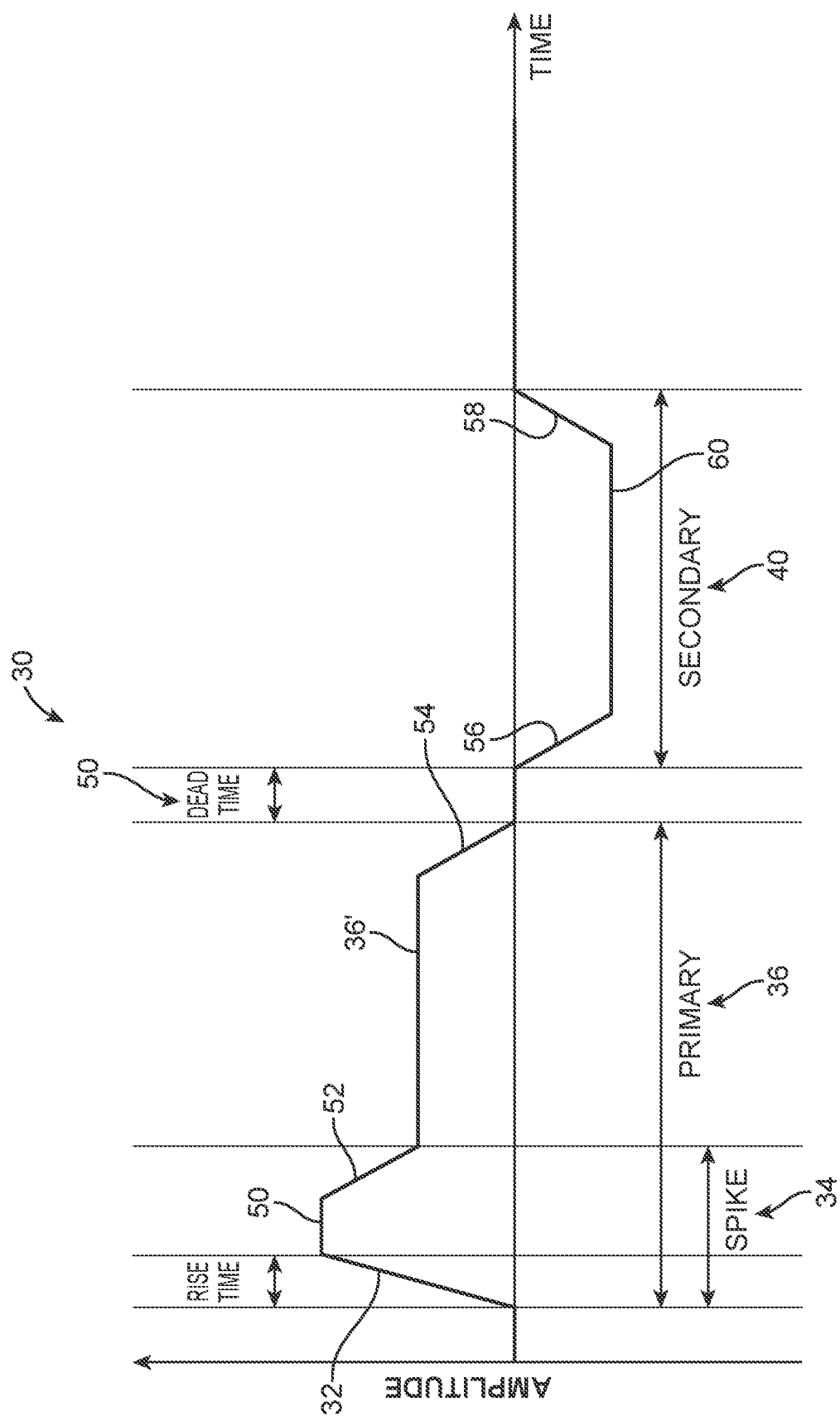
FIG. 3 shows a pulse waveform diagram illustrating phases of one variation of an electrical pulse output by the neuromodulation device as a simplified waveform with timing measurements.

FIG. 3 graphically illustrates an individual representative pulse waveform 30 with each of the major phases of an electrical pulse output. The primary phase 36 is shown including the leading edge 32 of spike 34 over a relatively short rise time and the remainder 36' of the primary phase 36 where the intensity of the spike 34 is significantly greater than an average intensity of the primary phase 36 and where the intensity of the remainder 36' is significantly lower than the intensity of the spike 34. The optional dead time 38 period, if included may follow the primary phase 36 and have an output amplitude of zero. This may then be followed by an optional secondary phase 40 which may have its polarity opposite to that of the primary phase 36, as shown.

The transition or edge rise and fall times are measured as the time from, e.g., 10% to 90% of the change from initial to final level. Widths are measured as the time from, e.g., the 10% level on the rising edge to the 10% level on the falling edge. The illustration of the pulse waveform 30 is intended to be illustrative of the relative shape of the waveform with its timing measurements. Hence, the amplitudes during the spike 34, primary 36 and secondary 40 phases of the pulse waveform 30 do not need to be held constant as shown in FIG. 3. Any pulse shape such that the spike 34 has a relatively fast rise time and high peak amplitude, and the typical amplitude during the remainder 36' of the primary phase 36 after the spike 34 is significantly less than the spike 34, may satisfy the requirements for an effective pulse waveform 30. For example, if it is easier for the pulse generating or control electronics to produce, the primary 36 and secondary 40 phases may be comprised of, e.g., piecewise segments of exponentially decaying waveforms (e.g., due to capacitor discharge or inductor decay), piecewise linear, trapezoidal, or any other shape which meets the described criteria.

The spike 34 itself may be shaped as, e.g., a half-sine wave, sine, parabolic, or similar waveform, as it is not necessary for it to have a constant level (e.g., "flat top"), although it is desirable if the slew rate during most of the rising edge is relatively constant.

Additionally, the transitions between the spike 34, primary 36, dead time 38, secondary 40, and OFF do not need to have rapid rise and fall times, or in any case the rapid rise and fall times are not necessary for effectiveness. However, it is desirable to have a relatively rapid and/or fall time 52 at the end of the spike 34 to maximize patient comfort. Once the brief time at maximum amplitude 50 during the spike 34 has passed, it is unlikely that any high but sub-maximum amplitude would have a physiological effect; however, it may cause greater charging of the skin capacitance and thus skin discomfort and for that reason it is desirable for the spike 34 to transition to the lower level during the remainder 36' of the primary phase 36 relatively quickly. The fall time 54 at the end of the primary phase 36, the rise time 56 from the dead time 38 to the secondary phase 40, and the fall time 58 from secondary phase 40 to the OFF state or inter-pulse interval are even less critical, and correspondingly the exact shape or slew rate during those parts of the pulse waveform 30 may be implemented in different ways while still having a therapeutically effective pulse shape as described herein.

Spike

Turning now to the individual portions of the pulse waveform 30, the spike 34 is comprised of a relatively high amplitude, short duration spike which has a leading edge 32 with a fast rise time. The effective electric field during the spike 34 is expected (for several reasons described in more detail below) to be high enough to be able to drive conformational changes of the cellular components which are targeted therapeutically directly, by the electrostatic forces acting on fixed charges or dipoles therein.

Without being bound by theory, it is likely that a relatively high electric field strength is needed in order to produce conformational changes and thereby modulate the physiological function of the target cellular components or molecules; hence, an initial spike 34 with an amplitude 50 which is significantly higher than the average amplitude during the primary phase 36.

While the rise time of the spike may vary, it remains relatively short. For instance, in one variation the spike rise time may be less than, e.g., 500 ns. In another variation the spike rise time may be less than, e.g., 100 ns, while in another variation the spike rise time may be less than, e.g., 50 ns, while in yet another variation the spike rise time may range between, e.g., 100 and 300 ns.

The spike 34 is specifically not necessarily intended to cause depolarization of nerve fibers as the threshold for nerve fiber depolarization by short electric field pulses is between, e.g., 0.75-2.98e-3 V-s/m (depending on fiber diameter). An effective spike 34 may have an amplitude of up to, e.g., 80-100 V, applied over the inter-electrode distance of, e.g., 5-20 cm, and duration of less than 10 us, or a duration of, e.g., 1-5 us, producing a sub-threshold value of less than, e.g., 0.01e-3 V-s/m, which is two orders of magnitude lower than that required for depolarization. Even a very intense spike of, e.g., 1 kV peak for 1 us, with a close electrode spacing of, e.g., 1 cm, has a sub-threshold value of, e.g., 0.1e-3 V-s/m, which is an order of magnitude lower than required for depolarization. With respect to the current of the spike, in one variation the peak spike current may be at least 30 mA while in yet another variation, the peak spike current may be at least 80 mA.

In one variation, the peak spike voltage divided by the electrode spacing may be at least 8 V/cm. In another variation, the peak spike voltage divided by the electrode spacing may be at least 50 V/cm, while in yet another variation, the peak spike voltage divided by the electrode spacing may be at least 100 V/cm.

The peak spike amplitude which may be safely used may be limited by the possibility of electroporation, and (in the case of high pulse repetition rates) by total pulse energy delivered to tissue. The electroporation threshold may be higher than, e.g., 1 kV/cm for pulses of 100 us or shorter duration. Much lower spike-induced field strengths, on the order of, e.g., 8-50 V/cm, are found to be therapeutically effective.

In one embodiment, the leading edge 32 of the spike 34 has a controlled slew rate, such that the rise time of the leading edge 32 corresponds to the time constant for the conformational changes of the target cellular components. The controlled slew rate allows any mobile charges (e.g., ions, molecular dipoles, etc.) with substantially shorter time constants to be mostly or substantially completely polarized by the applied field, and any charges with longer time constants to not be polarized yet, leading to maximum effect for a certain level of applied energy. The rise time is typically less than, e.g., 1 us, when targeting cellular membrane components, and more typically in the range of, e.g., 100-300 ns for pain relief. Significantly shorter rise times of less than, e.g., 50-100 ns, may be used to target intracellular components, for example in the nuclear membrane or mitochondrial membrane.

In addition to the high applied electric field, there are additional mechanisms which may be utilized to amplify the spike in vivo. Examples of such mechanisms may include the following:

The initial motion of charges in the immediate proximity to the cell membrane is likely to produce a very large field gradient across the membrane.

Electric double layers which may not have had the time to form during the spike (e.g., due to the slower time constants, above 20-100 us for double layers vs below 1 us for the leading edge and 5-10 us for the spike) and thus the reverse field produced by the double layers does not exist and cannot act opposite to the applied electric field.

For external or transcutaneous electrodes, the (large) skin capacitance formed between the electrode and the dermis (where the epidermis acts as the dielectric) has not charged yet during the spike.

Geometric focusing effects, for example, due to the curvature of cells and due to gaps formed by non-conductive elements such as the nodes of Ranvier which focus the electrical field into the gap.

As a result of these mechanisms, it is expected that the effective electrical fields present in the local environment of at least some of the macromolecules at the surface of nerve cells during the spike phase 34 of a pulse waveform 30 would be several orders of magnitude higher than the average field as calculated from electrode spacing, and would thus be in the effective range to drive conformational changes of macromolecules which may modify physiological function.

A number of non-spike pulse shapes which are non-rectangular pulses may be known in the art but do not produce the desired results as the spike 34 described herein. For example, capacitive discharge through a resistive load produces a pulse with an exponential decay waveform, the decay time constant of which is determined from the capacitance and the load resistance. Similarly, an inductor which starts out carrying a constant current and is then connected to a load would produce an exponential decay waveform. Since these methods of pulse shaping require relatively simple circuitry, exponentially decaying pulses are sometimes used. This also includes approximately-exponentially decaying pulses produced by a capacitor or inductor releasing its stored energy into a complex load impedance (such as the combination of electrodes and body) rather than a resistive load, or similar pulses produced by more complex circuitry.

Figure 4:
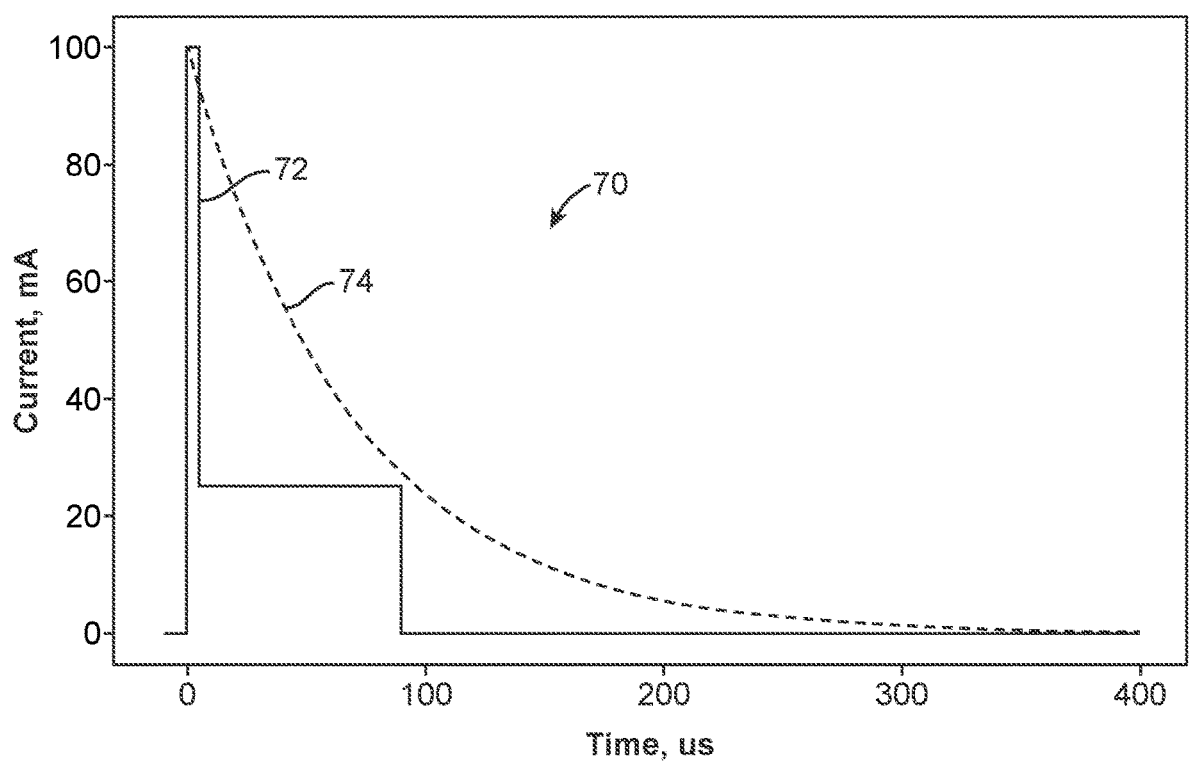
FIG. 4 shows a comparison between a spike waveform and an exponential waveform.

However, when comparing the spike 34 to an exponential waveform, some of the characteristic differences in the spike 34 become readily apparent. For instance, FIG. 4 shows a comparison graph 70 between a spike waveform 72 and an exponential waveform 74 for comparison. The spike waveform 72 has a t(spike) 5 us, I(spike) 100 mA, t(primary) 100 us, I(primary) 25 mA while the exponential waveform 74 has a I(peak) 100 mA and t(half width) 50 us.

While an exponential waveform 74 appears to share similar characteristics with the spike waveform 72 in that they start with an initially high intensity and then drop off over time, the exponential waveform 74 differs from the spike waveform 72 in that the rate of drop off is relatively slower, and consequently the total energy for an exponential waveform 74 pulse with similar duration and peak amplitude is much greater. The spike waveform 72 has a total energy per pulse of only 55 uJ, whereas the exponential waveform 74 has a total energy per pulse of 180 uJ, or approximately three times higher.

As another example, a 100 uF capacitor representing the physiological capacitance of the skin would be charged during a pulse to approximately 28.7 V by the spike waveform 72, and to 69.6 V during the exponential waveform 74.

Since the voltage across the skin capacitance is one of the main factors affecting patient comfort, the spike waveform is likely to be tolerated better at the same intensity, or allow a much higher intensity to be used with similar comfort.

It may not be necessary that the transition between spike 34 and primary phase 36 be as fast as the leading edge 32 of the spike 34. In one embodiment, the transition is a rapid linear transition 52 with a controlled fall time equal to the rise time of the leading edge 32 of the spike 34, but this is not required. Many variations in the transition between the spike 34 and primary phase 36 are possible which accomplish the same goal of relatively rapid transition using different profiles, as may be needed either by the generating method or for efficiency.

Figure 5A:
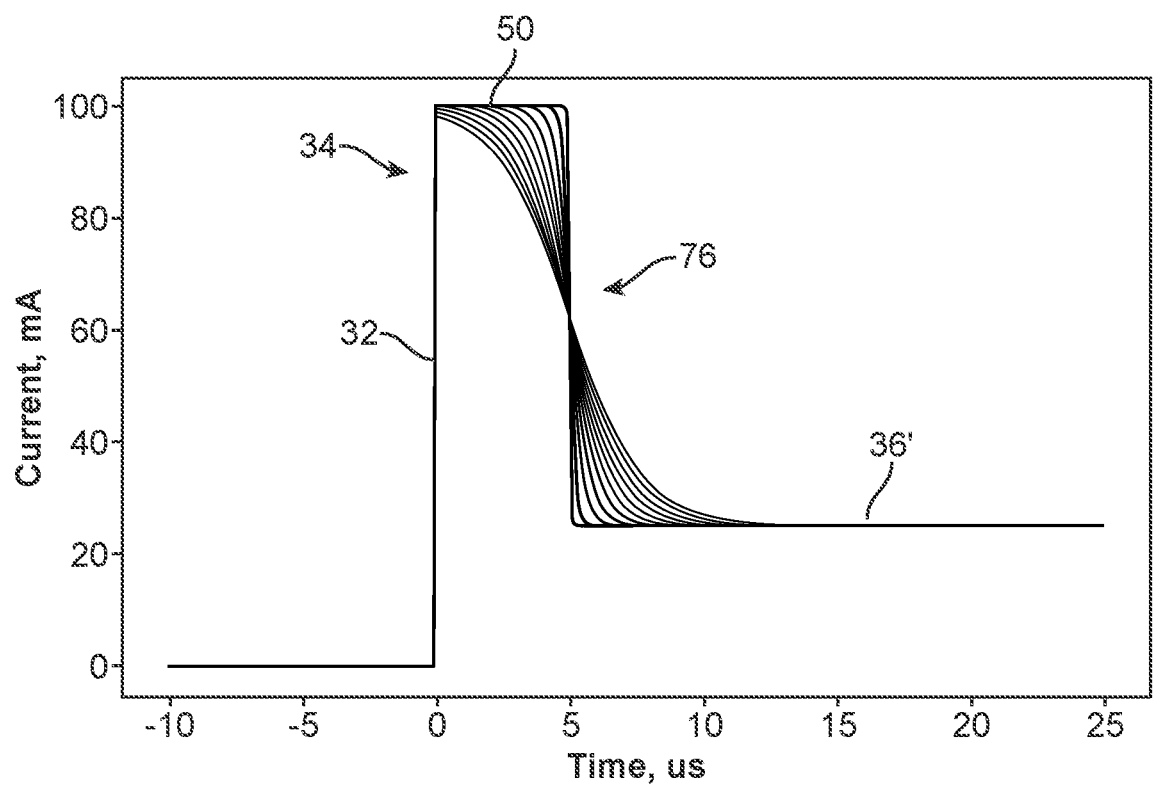
FIG. 5A shows examples of details of the spike portion of a family of waveforms with different times to transition.
Figure 5B:
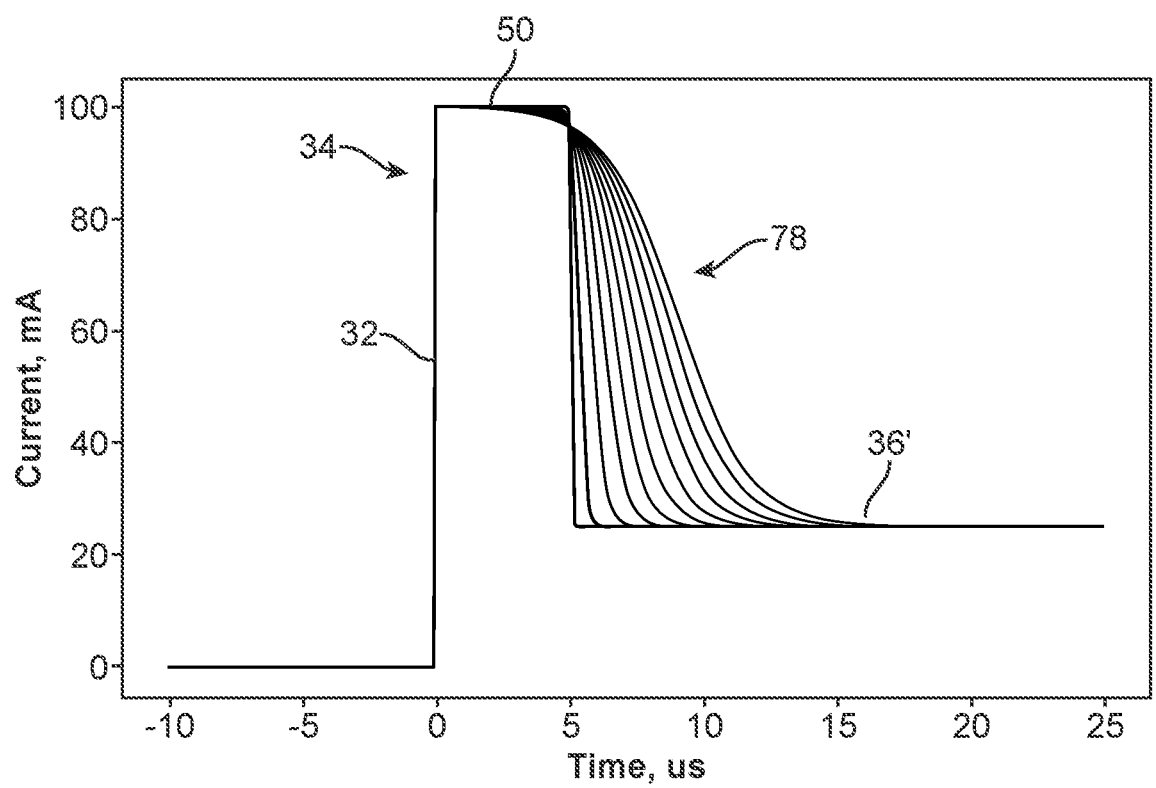
FIG. 5B shows examples of details of the spike portion of a family of waveforms with different times to transition except where the width of the spike is held constant as the transition time varies rather than the width of the middle portion of the spike.

FIGS. 5A and 5B illustrate various examples transitions between the spike 34 and primary phase 36. For example, FIG. 5A shows a detail of the spike portion 34 of a family of waveforms all having t(spike) measured at half height of, e.g., 5 us, and with different times to transition from, e.g., 80% to 20%, of the difference between spike amplitude 50 and primary phase amplitude. The transition curves 76 shown are sigmoid or logistic function curves with transition times ranging between, e.g., 0 and 7.5 us, for different curves in the family. These particular functions are shown as illustrations. Both this and any other form of transition, e.g., linear, truncated exponential, gaussian or truncated gaussian, sine or truncated sine, and with any transition time significantly shorter than the width of the primary phase, would be suitable embodiments.

FIG. 5B shows another detail of examples of transitions between the spike 34 and primary phase 36. In this example, the spike portion of a family of waveforms all have t(spike) measured at, e.g., 90% height of 5 us, and with different times to transition from, e.g., 80% to 20%, of the difference between spike amplitude and primary phase amplitude. The transition curves 78 shown are similar to the transition curves 76 in FIG. 5A, except that the width of the spike top is held constant as the transition time varies, rather than the width of the middle of the spike. Similarly, this and any other specific form of transition, with any transition time significantly shorter than the width of the primary phase, would be suitable embodiments.

In yet another variation, although a single spike 34 is illustrated in the waveform 30, for example in FIG. 3, multiple spikes may be transmitted at or near the beginning of the waveform 30. Alternatively, one or more spikes may also be transmitted at or near the beginning of the secondary phase 40 as well. These spikes during the secondary phase 40 may be opposite in polarity of the initial spikes during the primary phase 36.

Primary Phase

Following the spike 34, the remainder 36' of the primary phase 36 of the pulse 30 is less likely to be able to directly drive conformational changes, since the amplitude is relatively too low, and also various capacitances such as skin capacitance or electric double layer capacitance at cell membranes have had sufficient time to charge or begin charging, thereby reducing the effective field in the vicinity of the target macromolecules.

However, while the primary phase 36 may be important for optimum effect, a pulse 30 which includes only the spike 34 may be likely to be less effective. The primary phase 36 also serves to maintain, rather than produce, the conformational changes. If the spike 34 has a field which is large enough that it can quickly move the charged parts of some macromolecules, the remainder of the primary phase 36' has a weaker field which cannot move them quickly yet is sufficient to hold them in place.

In essence, the initial spike 34 causes any desired conformational changes, and the electrical field during the rest of the primary phase 36 maintains the changed conformation. Additionally, the maintenance of a field with the same polarity after the major conformational changes have occurred would cause the slower migration of counterions which would balance the charge redistribution caused by the conformational changes, and act to stabilize or "freeze in" the modified conformation for a longer period of time.

In some embodiments, the primary phase 36 may have a duration and intensity similar to the primary phase used in conventional transcutaneous electrical nerve stimulation (TENS). In that case, the described effects in this section may occur simultaneously with, and overlap, the TENS mechanisms of action such as the "pain gate" theory (Melzack and Wall 1965) or the centrally-acting endorphin mechanism (Salar 1981). Thus the output of the neuromodulation device described herein may be considered as a hybrid "spike plus TENS" mode if the primary phase has a duration and intensity sufficient to make it effective as a TENS pulse. In other embodiments, the primary phase 36 may be either too short or have too low an amplitude to be effective as a TENS pulse, resulting in a "pure spike" mode.

The average amplitude of the primary phase 36 only needs to be a fraction of the peak amplitude 50 of the spike 34. For example, in one variation the primary phase average amplitude may be less than 0.5 times the peak spike amplitude. In another variation the primary phase average amplitude may be less than 0.25 times the peak spike amplitude. However, as the skin capacitance and electric double layer capacitances are charging throughout the primary phase 36, this accumulating charge reduces the effective field at the target cellular components, and thus the amplitude should not be set too low. Very long duration of the primary phase (e.g., 500-1000 us) may lead to direct activation of muscle fibers leading to involuntary muscle contractions, and high currents combined with medium to long duration may lead to charging of the skin capacitance to an uncomfortable level (e.g., >50V per electrode). In practice the primary phase amplitude and duration may be set as high as is tolerable to the user, from a sub-sensory (imperceptible) level to a "strong but comfortable" level with amplitude and duration similar to TENS.

In one embodiment, the primary phase average current is between, e.g., 1 and 100 mA, and the duration is between, e.g., 20 and 500 us. In yet another embodiment, the primary phase average current is between, e.g., 10 and 50 mA, and the duration is between, e.g., 80 and 120 us. These values are appropriate for medium sized electrodes with pad area, e.g., 25-50 cm$^2$, spaced, e.g., 5-10 cm apart. These values may be modified to maintain similar current density and field strength if the electrode configuration changes significantly. In other variations, the electrodes may have a contact area of, e.g., 5 to 100 cm$^2$ per pad.

Secondary Phase

During the secondary phase (if present), the direction of the electrical field is reversed to allow for a controlled discharge of the skin and tissue capacitances and so that a net charge per pulse may be minimized ("zero net charge per pulse"). A non-zero net charge per pulse is a concern because of the possibility for ions (e.g., metal ions from the electrodes) to migrate into the tissue over time (via iontophoresis), causing a negative physiological reaction. There is also a concern about the undesired migration of ions which are found in tissue, e.g., ions which have a signaling function such as calcium, diacylglycerol, inositol triphosphate, etc. as well as various charged proteins (especially those with high charge/mass ratio).

In one variation, the primary phase may be followed by the secondary phase of opposite polarity where the net charge per pulse of the secondary phase is less than, e.g., 10% of the total charge during the primary phase. In another variation, the residual voltage at the end of the secondary phase may be less than, e.g., 10% of the peak voltage during the primary phase.

Additionally, for patient comfort it is desirable to discharge the skin capacitance faster that it would normally self-discharge as leaving the skin capacitance charged to a high voltage for an extended period of time may lead to activation of cutaneous sensory receptors found in the dermis or epidermis, including the cutaneous mechanoreceptors, nociceptors and thermoreceptors. This can be perceived as a sensation of tingling, paraesthesia ("pins and needles"), pinching or burning sensation in the skin under the electrodes, which may be uncomfortable especially at high stimulation levels. To limit the skin sensation under the electrode and improve patient comfort, it is desirable to limit the voltage to which the skin capacitance is charged, and to limit the duration for which the skin capacitance remains charged by discharging it using the secondary phase 40 of the pulse.

In another embodiment, during the secondary phase 40 of the output pulse the device may act as a current-limited constant impedance or current-limited short circuit rather than a current source. This allows any capacitances which were charged during the primary phase 36 (e.g., electrode-skin capacitance, or cell membrane capacitances in tissue) to discharge in a controlled way, without being able to drive new charges. This mode is shown in FIG. 4 (described in further detail below) where the current decays exponentially during the secondary phase 40, consistent with the relaxation behavior of an RC circuit provided by the load. In this example, the load resistance is high enough that the device current limit is not reached. If a lower resistance were connected then the device would limit current during part of the secondary phase 40. The secondary phase 40 duration may be chosen to be long enough so that the ending voltage is near zero. With typical electrode and tissue parameters, a duration of, e.g., approximately 3-5 times the primary phase duration, allows for a near-zero ending voltage.

In another embodiment, the secondary phase 40 of the output pulse may be a current source and the amplitude and duration may be chosen so that the net charge during the secondary phase 40 is approximately equal to the net charge during the primary phase 36, and/or so that the residual voltage after the secondary phase 40 is near zero.

The secondary phase amplitude 60 may be chosen so as to allow relatively rapid discharge (for patient comfort) yet limit the peak currents. In another embodiment, the maximum amplitude during the secondary phase 40 may be chosen to be approximately equal to the average amplitude during the primary phase 36.

If the secondary phase is not present, the skin and tissue capacitances may self-discharge once the application of the primary phase 36 is removed. Since the self-discharge is relatively slower than the external or driven discharge (as would be provided by a secondary phase 40), this allows the effects of the electrical field to last longer (or tail off over a longer period) at the cost of potentially reduced patient comfort at high stimulation amplitudes. In another embodiment, the secondary phase 40 may be omitted if the stimulation is at a very low or sub-sensory (imperceptible) amplitude.

In yet another embodiment, successive pulses may be alternated in direction. In other words, each pulse with a primary phase with one polarity may be followed by subsequent pulse with an identical shape but reversed polarity. Balancing charges between the primary and secondary phase of a pulse to a net zero charge may be difficult and migration of ions may occur due to shape asymmetry within a pulse even if the net charge at the electrodes is zero. Yet alternating pulses may allow for effectively zero migration of ions per pair of pulses regardless of asymmetry or non-zero net charge per pulse. This may apply particularly if the secondary phase is omitted, leading to significant net charge per pulse.

In yet another embodiment, a running total of pulses of each direction may be approximately equal even if they do not strictly alternate direction. For example, a first group of several pulses of the same direction may be followed by a second group with an equal number of pulses having the opposite direction, so that the net number of unbalanced pulses is always less than the group size. Such a configuration may be desirable in some of the pulse train modes.

Given the parameters of the pulse waveform 30, the pulse timing parameters may vary. For instance, in one embodiment, the pulse timing parameters may range according to the following:
t(rise time) 10-500 ns
t(spike) 1-20 us
t(primary) 50-500 us
t(dead time) 0-100 us
t(secondary) 50-2000 us In another embodiment, the pulse timing parameters may range according to the following:
t(rise time) 200-300 ns
t(spike) 4-10 us
t(primary) 80-120 us
t(dead time) 20-60 us
t(secondary) 80-480 us In yet another embodiment, the pulse timing parameters may range according to the following:
t(rise time) 300 ns
t(spike) 4.6 us
t(primary) 90 us
t(dead time) 40 us
t(secondary) 360 us (current-limited external discharge, exponentially decaying amplitude)

EXAMPLES

As mentioned above, FIG. 6 illustrates an example of a pulse waveform 80 showing the electrical output of an exemplary implementation recorded where the device output was connected to a test load simulating a human body, as described in the AAMI NS4 standard. The test load comprised a 500 ohm resistor connected in series to a parallel combination of a 0.1 uF capacitor and 2700 ohm resistor. An oscilloscope was connected to measure voltage across the 500 ohm resistor, which may be converted to device output current as current=voltage/500 ohm (14 mA per vertical division, 50 us per horizontal division).

As shown, the pulse waveform 80 has leading edge 82 with a high intensity spike amplitude 84 which is followed by the primary phase 86. The secondary phase 88 follows having a secondary phase amplitude 90.

The pulse timing parameters for this example were as follows:
t(rise time) 300 ns
t(spike) 4.6 us
t(primary) 90 us
t(deadtime) 40 us
t(secondary) approximately 200 us (exponential decay)
The pulse parameters for this example were as follows:
spike amplitude 62 mA (approximately)
primary phase amplitude 30 mA (outside of spike, approximately)
secondary phase amplitude −28 mA (peak, approximately)

The timings and amplitudes shown are appropriate for usage for low back pain with pad electrodes of approximately 20 to 50 cm$^2$ contact area.

Figure 6:
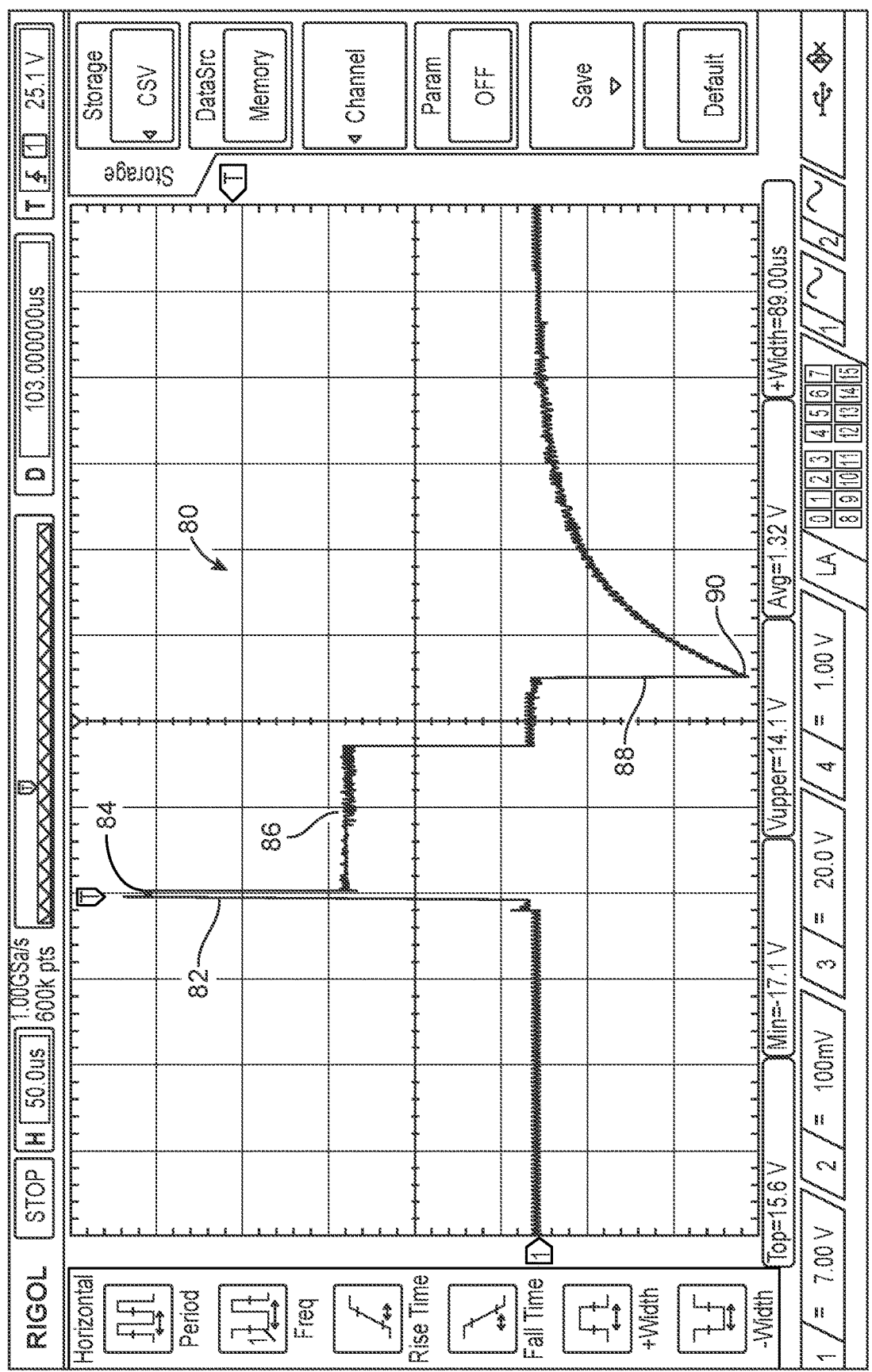
FIG. 6 shows an example of the electrical output of an implementation of the neuromodulation device as recorded.
Figure 7:
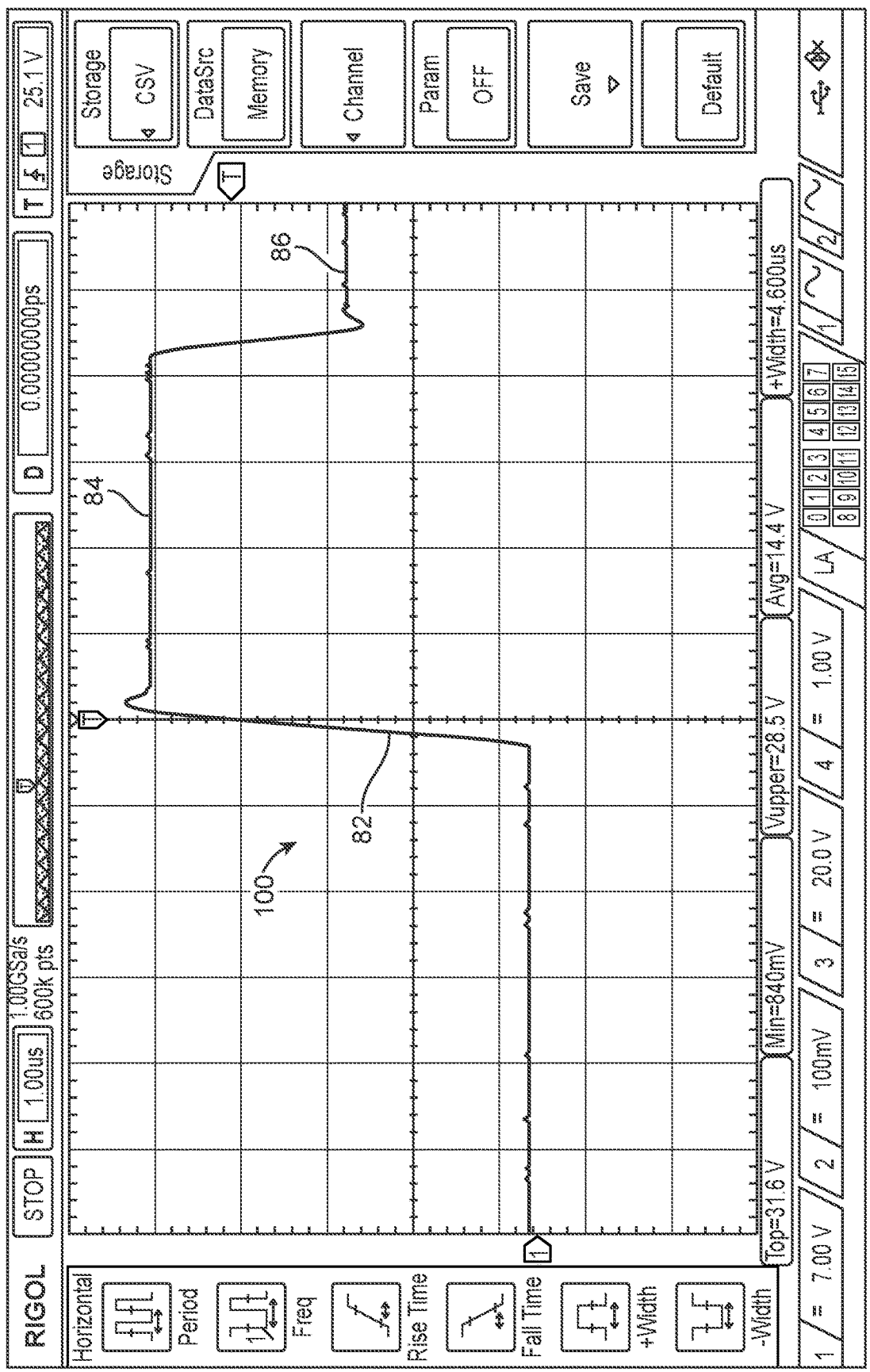
FIG. 7 shows an example of the spike portion of the waveform.
Figure 8:
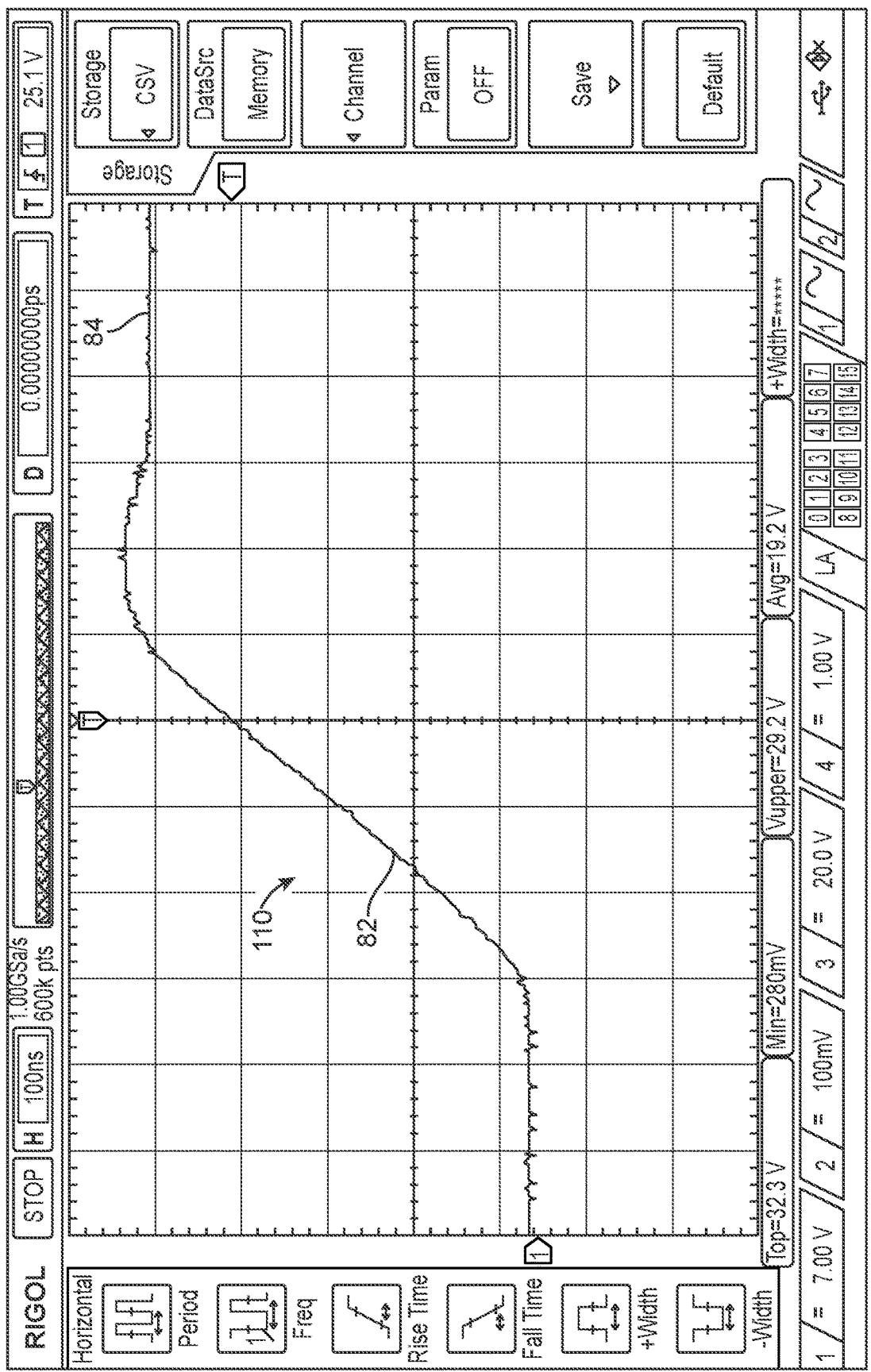
FIG. 8 shows an example of the rise time portion of the waveform.

FIG. 7 shows a detail 100 of the spike portion of the pulse waveform 80 of FIG. 6. The recording method was the same except for the horizontal scale (1 us per horizontal division). The spike duration was approximately 4.6 us. FIG. 8 shows a finer detail 110 of the spike portion of the pulse waveform 80 of FIG. 6 with details of the leading edge 82 rise time portion. The recording method was the same except for the horizontal scale (100 ns per horizontal division). The rise time was approximately 300 ns.

Figure 9:
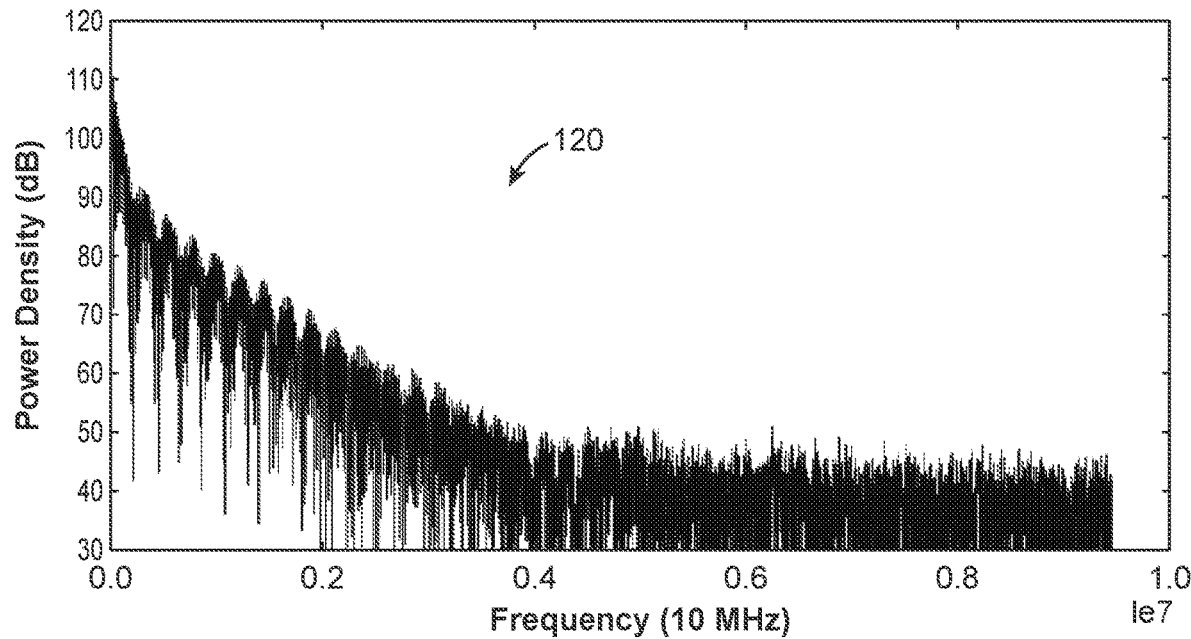
FIG. 9 shows an example of the spectrum of a waveform.

FIG. 9 shows the spectrum 120 of the waveform 80 shown in FIG. 6. The spectrum 120 was calculated by recording a 600 k sample waveform sampled every 1 ns and digitized to 8 bits, zero-padding to 10M points and calculating the FFT. The horizontal axis shows frequency in units of 10 MHz. The vertical axis shows power density in dB (calculated based on the measured voltage across the 500 ohm sense resistor in the test load), thus the vertical axis can be interpreted as relative power density. The noise floor is approximately 35 to 40 dB. There is significant output at all frequencies 0 to 4 MHz, with rolloff at approximately −20 dB per decade. From the simulation, the same pattern is expected to continue to frequencies over 4 MHz as well, but it is below the noise floor in the present measurement.

Figure 10:
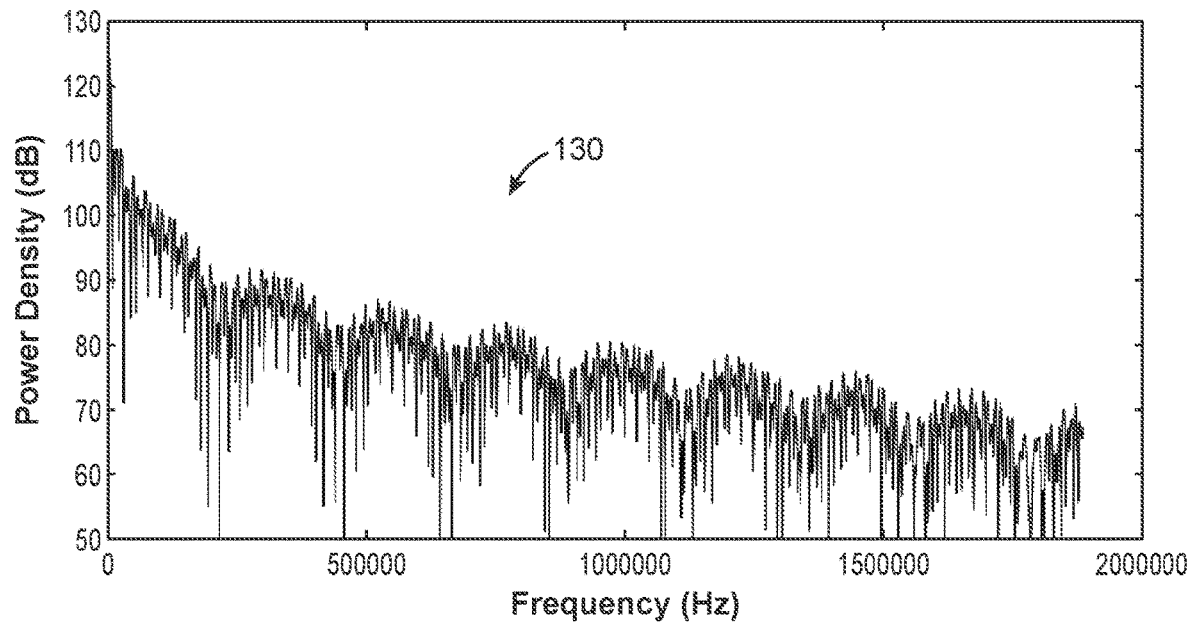
FIG. 10 shows an example of the spectrum with the frequencies ranging from 0 to 2 MHz.

FIG. 10 shows a detailed view 130 of the spectrum from FIG. 9 between the frequencies of 0 to 2 MHz. There is a pattern of lobes spaced about every 4 kHz corresponding to the effective pulse width (both phases) of approximately 200-250 us, and lobes spaced about every 200 kHz corresponding to the width of the spike of approximately 4.6 us. The conformational changes in macromolecules driven by an electrical field can be seen in the dielectric spectrum of tissue, as shown for example in FIG. 8. Specifically, conformational changes correspond to the beta dispersion, which occurs at frequencies of 0.1 to about 100 MHz. The very high end of the beta dispersion range is likely to correspond to the rotation of soluble or globular proteins, whereas the very low end of that range is likely due to membrane charging effects. Conformational changes of transmembrane proteins (such as receptors) or membrane anchored proteins would be expected to have intermediate frequencies of approximately 1-10 MHz.

This is further supported by the example of an experiment (Liu D S, Astumian R D, Tsong T Y. Activation of Na+ and K+ pumping modes of (Na, K)-ATPase by an oscillating electric field. Journal of Biological Chemistry 1990; 265 (13):7260-7267) in which the transmembrane protein (Na, K)-ATPase was activated solely by an applied electric field at 1 MHz and 20 V/cm, which was found sufficient to produce conformational changes which cause ion pumping in the absence of the native energy source (ATP). By analogy, a suitable pulsed applied field with components in the 1-10 MHz range can produce conformational changes in receptors which cause them to act as though a ligand was present, even in the absence of a native ligand; or, as a more subtle effect, to modify the receptor-ligand kinetics for example binding constants or binding cooperativity thus producing a stronger or weaker receptor response to the same ligand concentration.

One possible therapeutic target of the device and method described is ion channels, such as voltage-gated sodium channels, or voltage-gated channels for other ions such as potassium or calcium. The effect on sodium channels may be to shift the threshold transmembrane potential for activation of the channel, the threshold for inactivation, and/or to change the time to activation or inactivation of the channel. Voltage-gated sodium channels have an α-subunit with four repeat domains, labeled I through IV, each containing six membrane-spanning segments, labeled S1 through S6. The S4 segment carries a large positive charge and acts as a sensing element for transmembrane voltage. The time constants for activation and inactivation with large transmembrane voltages (>+−80 mV) are on the order of 100 us, much shorter than for low voltages, but still relatively long compared to the time scale of the typical device output pulses. An external electric field with a duration of a few us such as during the spike is unlikely to be able to directly cause activation or inactivation, but it may shift the activation or inactivation threshold substantially if it occurs during the propagation of a natural nerve impulse.

Another possible therapeutic target is transmembrane proteins, particularly transmembrane receptors, and even more particularly receptors in the G-protein coupled receptor (GPCR) family, some of which are closely associated with pain and pain-related disorders. Some specific GPCRs relevant to pain which may be targeted by the present neuromodulation device may include, e.g., opioid receptors (five major subtypes including delta, kappa, mu, zeta, and nociceptin receptors; for sensing endogenous opioids including dynorphins, enkephalins, endorphins, endomorphins and nociceptin), and neurokinin 1 receptor (for sensing Substance P).

Yet another possible therapeutic target is membrane-anchored glycoproteins and proteoglycans which have attached long polysaccharide chains that are negatively charged under physiological conditions due to the occurrence of charged groups such as sulfate or uronic acid groups. These molecules are involved in a number of processes related to nerve growth and differentiation, receptor cycling, and formation of lipid rafts which affect receptor sensitivity, and which would affect nociception and pain signal transduction. The significant negative charge density on the polysaccharide chains which are located outside of the cell membrane is expected to make them experience particularly large conformational changes in response to an applied electric field.

Figure 11:
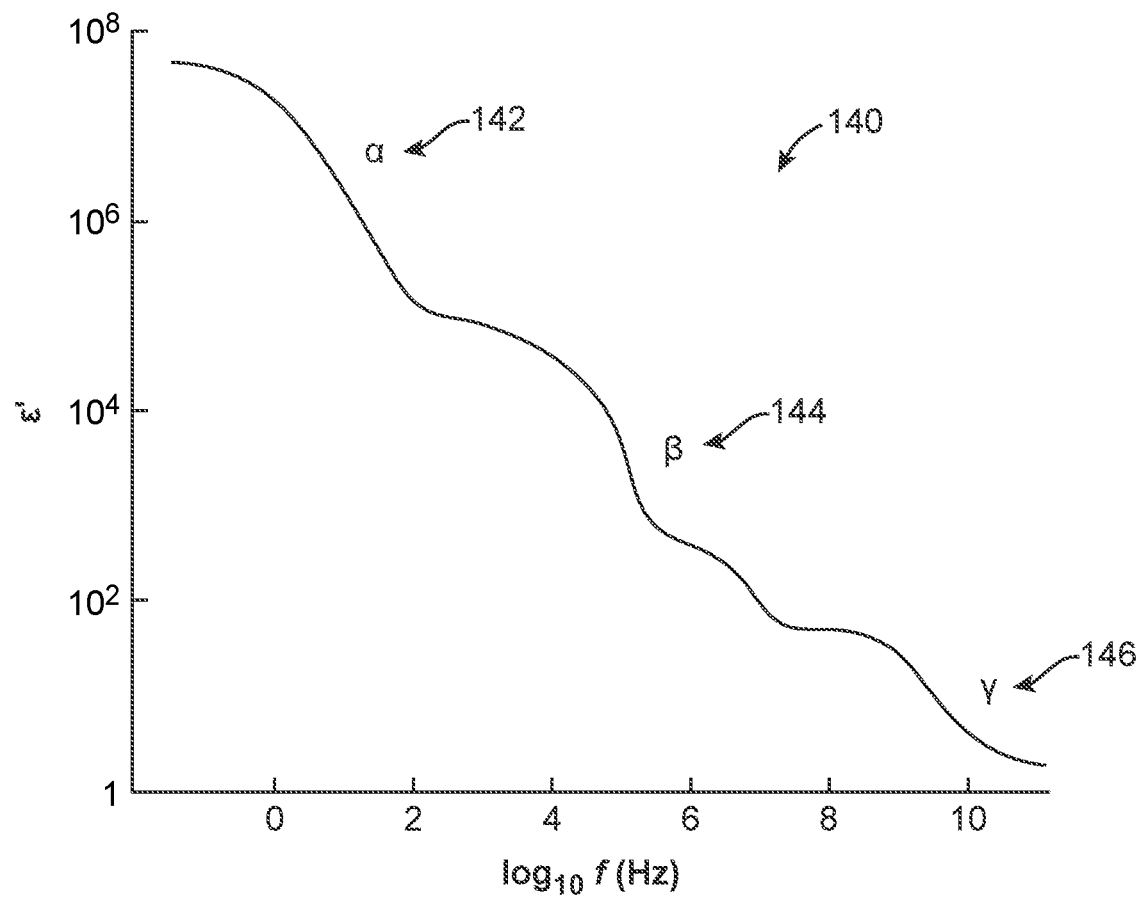
FIG. 11 shows the dielectric permittivity of biological tissue as a function of frequency.

FIG. 11 illustrates in graph 140 an example of the dielectric permittivity of biological tissue as a function of frequency (Ronald Pethig, Electrical Properties of Biological Tissue, chapter 6 in Andrew A. Marino (ed), Modern Bioelectricity, Marcel Dekker, New York, 1988). This is an idealized description that shows the typical features in the spectrum and accordingly does not correspond to a specific tissue type and the magnitude and position of the features is approximate. The α-dispersion 142, β-dispersion 144, and γ-dispersion 146 (steps down in permittivity) are indicated as these correspond to mobile charges in tissue which have different time constants and are due to different biophysical phenomena, as indicated.

The α-dispersion 142 is associated with interfacial polarizations associated with electrical double layers and surface ionic conduction effects at membrane boundaries. The frequency is in the ml-Hz (milliHertz) to kH range, and the permittivity (polarizability) is extremely high (relative permittivity up to 1e+7) due to the large number of mobile ions and large area of membranes which may form electric double layers.

The β-dispersion 144 is produced by two independent mechanisms with similar time constants, the charging of cell membrane capacitances, and the rotation and other conformational changes of charged macromolecules. The frequency is 0.1 to about 100 MHz.

The γ-dispersion 146 is primarily due to dipolar relaxation of water at microwave frequencies, 25 GHz for free water at body temperature, and much lower (down to 1 GHz) for water associated with proteins in tissue.

In yet another example, the devices and methods described herein may be used to treat a number of various conditions such as treatment of pain including chronic or acute pain in human subjects. Examples of the types of pain which may be treated with the devices and methods herein may include, e.g., somatic pain, musculoskeletal pain, mechanical pain, neuropathic pain, phantom pain, inflammatory pain, postoperative pain, allodynia, complex regional pain syndrome, fibromyalgia, etc.

The degree and duration of pain relief may depend on the degree to which any underlying injury or other pathology has healed. In the case of acute injury, the pain relief may be only temporary and may require repeated or continuous treatment. On the other hand, in the case of chronic pain where the original injury is fully healed, treatment using the device and methods herein may provide durable pain relief.

Generally, during use two or more electrodes of the device may be placed upon the surface of the body such that the current between the electrodes passes transcutaneously through the painful area or through some of the major sensory nerves which innervate the painful area.

Figure 12A:
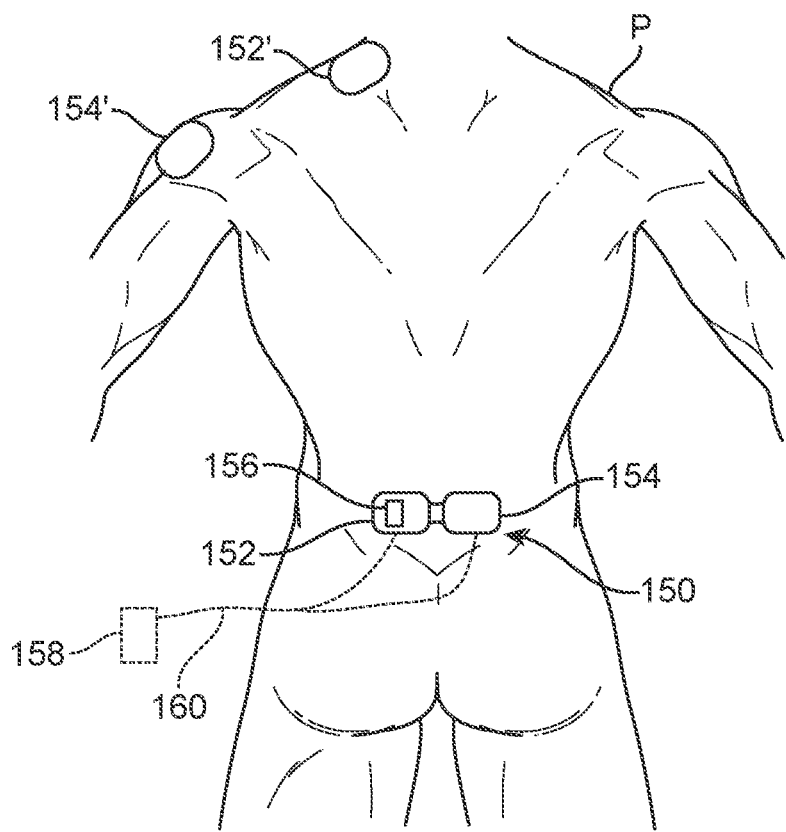
FIGS. 12A to 12D show examples of electrode placement over various regions of the body for different types of treatments.

For example, in one method for treating low back pain as shown in FIG. 12A, the electrodes 152, 154 of the device 150 may be placed symmetrically across the spine of a patient P at the level of the major nerves which innervate the area of the pain. In this mode the stimulation may be applied to the dorsal root ganglia of the spinal nerves. In one variation as described above, the control electronics/power supply 156 may be attached directly to the device 150. The control electronics/power supply 156 may directly control the waveforms transmitted through the electrodes 152, 154 while in other variations, a separate controller in wired or wireless communication with the electronics/power supply 156 may instead control the waveforms. In other variations, the control electronics/power supply 158 may be coupled wirelessly or via connecting elements 160, e.g., conductive wires, as a unit separate from the electrodes 152, 154.

In yet another variation, the electrodes may be placed vertically alongside the spine, e.g., above and below the level of the major nerves which innervate the area of pain. In this mode the stimulation is applied to the spinal nerves at a depth that depends on the electrode spacing.

Figure 12B:
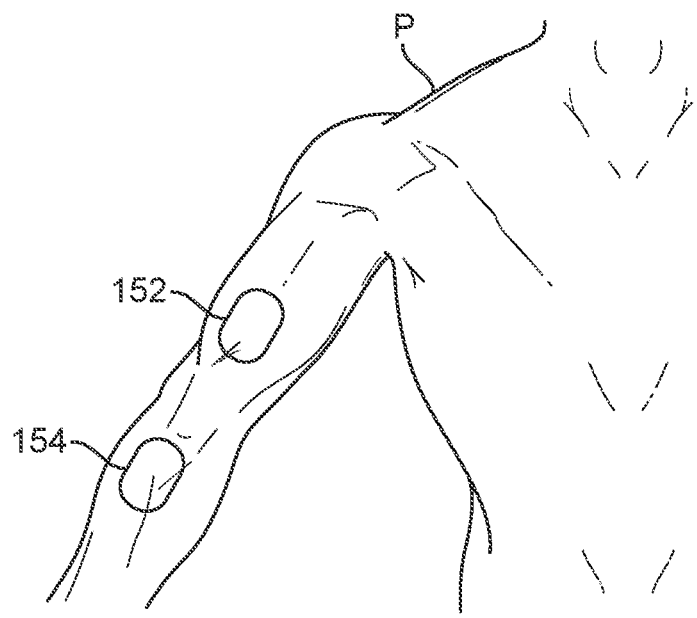

In yet another variation, the electrodes 152, 154 may be placed longitudinally along a major nerve which innervates the area of the pain, for example, the ulnar nerve below the elbow for wrist pain, as shown in FIG. 12B. This is particularly effective where the nerve is close to the surface.

In yet another variation, the electrodes may also be placed in a longitudinal manner along the major nerves such that the electric current from one electrode to the other intersects the nerves at an oblique angle. For example, placing one electrode 152' on the back of the neck at the top of the trapezius and another electrode 154' at the outside of the deltoid causes the current to intersect most of the nerves coming from the brachial plexus, and is effective for shoulder pain, as shown in FIG. 12A.

Figure 12C:
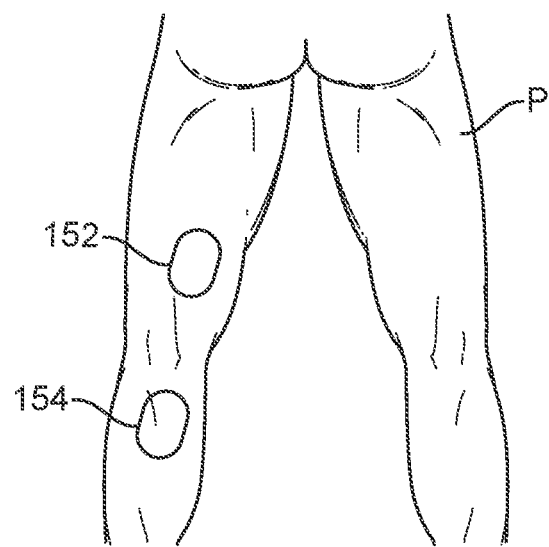

In yet another variation, the electrodes 152, 154 may be placed across the major nerves proximally to the area of the pain, for example across the thigh for knee pain, as shown in FIG. 12C.

Figure 12D:
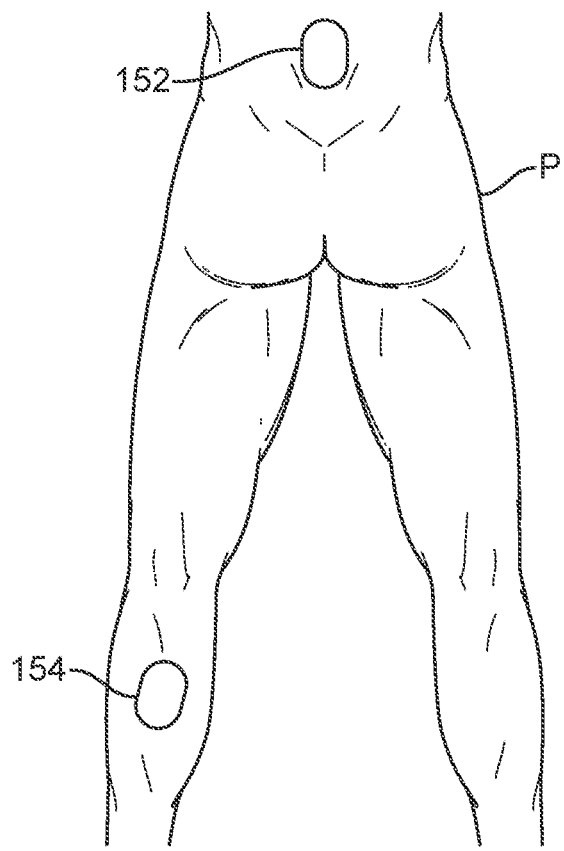

In yet another variation, the electrodes 152, 154 may be placed along the major nerves one proximally to the area of the pain and one distally to the area of the pain, for example, one at the side of the spine at the root of the major nerve and the other along the limb. An example of this placement is one electrode 152 at the lumbar spine L5-S1 and another electrode 154 on the calf, for sciatic nerve pain, as shown in FIG. 12D.

In yet another variation, the electrodes may be placed across the area of the pain, which produces the most localized type of pain relief.

According to one method for using the device for pain relief, the device may be used for approximately, e.g., at least 15 minutes, at a time. Alternatively, the device may be used for approximately, e.g., 30 to 90 minutes, at a time. Sessions of at least, e.g., 45 minutes, appear may be applied to provide optimum pain relief, and sessions over, e.g., 90 minutes, may have diminishing results.

The treatment may be repeated multiple times per day as needed. It may be unnecessary to repeat a treatment more often than, e.g., once every 3-4 hours.

Additionally, the treatment may be applied, e.g., at least once daily for a certain number of days (e.g., at least 10 days), even if the pain level is low or absent on a particular day. This may prevent the pain from worsening or recurring.

For example, one typical course of treatment for chronic low back pain may be 60 minutes once or twice daily for two weeks.

In another example for treating low back pain, a hybrid mode for treatment may be utilized with the following parameters: pulses with t(rise) 300 ns, t(spike) 4.6 us, t(primary) 90 us, t(secondary) 360 us (with exponential decay), spike peak amplitude 60 mA, primary amplitude 30 mA, repeated at 40-130 Hz, pulses with alternating polarity. Two electrodes with area 25-50 cm$^2$ each, placed across the spine at the same level as the pain.

In another example for treating pain, a sub-sensory mode for long-term or continuous use may be utilized with the following parameters: pulses with t(rise) 300 ns, t(spike) 2 us, t(primary) 150 us, t(secondary) 600 us (with exponential decay), spike peak amplitude 60 mA, primary amplitude 5 mA, repeated at 80-100 Hz in bursts with 5-30% burst duty cycle, pulses with alternating polarity. Two electrodes with area 25 cm$^2$ each, placed across the location of the pain, or longitudinally along the major nerve leading to the location of the pain.

In another example for treating pain, a sub-sensory mode for high intensity pain relief may be utilized with the following parameters: pulses with t(rise) 100 ns, t(spike) 5 us, t(primary) 200 us, no secondary phase, spike peak amplitude 200 mA, primary amplitude 15 mA, repeated at 20-160 Hz, pulses with alternating polarity. Two electrodes with area 25 cm$^2$ each, placed 5-10 cm apart across the location of the pain.

In another example for treating pain, a spike-only mode for inflammation may be utilized with the following parameters: pulses with t(rise) 100 ns, t(spike) 1 us, t(primary) 30 us, t(secondary) 120 us (with exponential decay), spike peak amplitude 80 mA, primary amplitude 10 mA, repeated at 200-500 Hz, pulses with alternating polarity. Two electrodes with area 25 cm² each, placed 5-10 cm apart across the location of the inflammation.

The applications of the devices and methods discussed above are not limited to pain treatment but may include any number of further treatment applications. Moreover, such devices and methods may be applied to other treatment sites within the body. Modification of the above-described assemblies and methods for carrying out the invention, combinations between different variations as practicable, and variations of aspects of the invention that are obvious to those of skill in the art are intended to be within the scope of the claims.

What is claimed is:

1. A neuromodulation treatment apparatus, comprising:
a controller programmed to transmit one or more pulse waveforms having a spike and a primary phase following the spike,
wherein the spike has a first amplitude of up to 100 V and which is independent of an effect of variations in load impedance and a first duration time of between 1-5 µs and the primary phase has a second amplitude which is also independent of the effect of variations in load impedance and a second duration time,
wherein the first amplitude is greater than the second amplitude and the first duration time is less than the second duration time such that the spike has an intensity which is greater than an average intensity of the primary phase, and
wherein an electric field of the spike has a strength sufficient to produce a conformational change in cellular components of a tissue region of interest and an electric field of the primary phase has a strength sufficient to maintain the conformational change induced by the electric field of the spike.

2. The apparatus of claim 1 wherein the spike has a total energy per pulse of 55 µJ.

3. The apparatus of claim 1 wherein the one or more pulse waveforms are applied over an inter-electrode distance of between 5-20 cm such that a sub-threshold value is 0.01e-3 V-s/m.

4. The apparatus of claim 1 wherein the one or more pulse waveforms are applied over an inter-electrode distance of 1 cm such that a sub-threshold value is 0.1e-3 V-s/m.

5. The apparatus of claim 1 wherein the spike has a rise time of less than 1 µs.

6. The apparatus of claim 1 wherein the spike has a rise time of less than 50 ns.

7. The apparatus of claim 1 wherein the spike has a rise time of less than 100 ns.

8. The apparatus of claim 1 wherein the spike has a rise time of less than 500 ns.

9. The apparatus of claim 1 wherein the spike has a rise time of between 100 and 300 ns.

10. The apparatus of claim 1 wherein the spike and the primary phase have the same polarity.

11. The apparatus of claim 1 wherein the primary phase has an average current of between 1 and 100 mA.

12. The apparatus of claim 1 wherein the primary phase has an average current of between 10 and 50 mA.

13. The apparatus of claim 1 wherein the primary phase has a duration time of between 20 and 500 µs.

14. The apparatus of claim 1 wherein the primary phase has a duration time of between 80 and 120 µs.

15. The apparatus of claim 1 wherein the controller is further programmed to transmit a dead time having a zero amplitude following the primary phase.

16. The apparatus of claim 1 wherein the controller is further programmed to transmit a secondary phase following the primary phase, wherein the secondary phase has a polarity opposite to a polarity of the primary phase to allow for a controlled discharge of a tissue region of interest.

17. The apparatus of claim 16 wherein the secondary phase has a net charge per pulse of less than 10% of a total charge during the primary phase.

18. The apparatus of claim 16 wherein the secondary phase has a residual voltage at an end of the secondary phase of less than 10% of a peak voltage during the primary phase.

19. The apparatus of claim 16 wherein the secondary phase has a third duration time of 3-5 times the second duration time.

20. The apparatus of claim 16 wherein the spike has a rise time of between 10-500 ns, the second duration time of between 50-500 µs, and a third duration time of the secondary phase of between 50-2000 µs.

21. The apparatus of claim 20 further comprising a dead time duration of between 0-100 µs between the primary phase and the secondary phase.

22. The apparatus of claim 16 wherein the spike has a rise time of between 200-300 ns, the second duration time of between 80-120 µs, and a third duration time of the secondary phase of between 80-480 µs.

23. The apparatus of claim 22 further comprising a dead time duration of between 20-60 µs between the primary phase and the secondary phase.

24. The apparatus of claim 16 wherein the spike has a rise time of 300 ns, the first duration time of 4.6 µs, the second duration time of 90 µs, and a third duration time of the secondary phase of 360 µs.

25. The apparatus of claim 24 further comprising a dead time duration of 40 µs between the primary phase and the secondary phase.

26. The apparatus of claim 1 wherein the controller is programmed to transmit a plurality of the pulse waveforms in succession.

27. The apparatus of claim 26 wherein successive pulse waveforms are alternated in direction from one another.

28. The apparatus of claim 26 wherein the plurality of waveforms is comprised of a first group of several pulses having a first polarity followed by a second group with an equal number of pulses having a second polarity opposite to the first polarity.

29. The apparatus of claim 1 wherein the controller is programmed to apply the one or more pulse waveforms to a tissue region between 30 to 90 minutes.

30. The apparatus of claim 1 wherein the controller is programmed to apply the one or more pulse waveforms to a tissue region for at least 15 minutes.

31. The apparatus of claim 1 further comprising a first electrode and a second electrode in electrical communication with the controller for transmitting the one or more pulse waveforms.

32. The apparatus of claim 30 wherein a peak voltage of the spike divided by a spacing between the first and second electrodes is at least 8 V/cm.

33. The apparatus of claim 30 wherein a peak voltage of the spike divided by a spacing between the first and second electrodes is at least 50 V/cm.

34. The apparatus of claim 30 wherein a peak voltage of the spike divided by a spacing between the first and second electrodes is at least 100 V/cm.

35. The apparatus of claim 30 wherein the first and second electrodes each have a contact area of 5 to 100 cm$^2$.

36. The apparatus of claim 30 wherein the first and second electrodes each have a contact area of 25 to 50 cm$^2$.

37. The apparatus of claim 1 wherein a peak current of the spike is at least 30 mA.

38. The apparatus of claim 1 wherein a peak current of the spike is at least 80 mA.

39. The apparatus in claim 1 wherein an average amplitude of the primary phase is less than 0.5 times a peak amplitude of the spike.

40. The apparatus in claim 1 wherein an average amplitude of the primary phase is less than 0.25 times a peak amplitude of the spike.

41. The apparatus of claim 1 wherein the controller is programmed to transmit one or more pulse waveforms having a plurality of spikes near or at a beginning of the primary phase.

42. The apparatus of claim 1 wherein the controller is programmed to transmit one or more pulse waveforms having a plurality of spikes near or at a beginning of the secondary phase.

43. The method of claim 1 wherein the electric field of the spike has a strength sufficient to produce a conformational change when the one or more pulse waveforms are delivered transcutaneously to the tissue region of interest from an external region of a body.

\* \* \* \* \*